US011505810B2

(12) United States Patent
Haushalter et al.

(10) Patent No.: US 11,505,810 B2
(45) Date of Patent: Nov. 22, 2022

(54) HOST CELLS AND METHODS FOR PRODUCING ALKYL LACTONE BY CYCLIZATION OF HYDROXYL FATTY ACID

(71) Applicants: Robert W. Haushalter, Emeryville, CA (US); Jay D. Keasling, Berkeley, CA (US)

(72) Inventors: Robert W. Haushalter, Emeryville, CA (US); Jay D. Keasling, Berkeley, CA (US)

(73) Assignee: The Regents of the University of California, Oakland, CA (US)

(*) Notice: Subject to any disclaimer, the term of this patent is extended or adjusted under 35 U.S.C. 154(b) by 0 days.

(21) Appl. No.: 16/810,655

(22) Filed: Mar. 5, 2020

(65) Prior Publication Data
US 2020/0385766 A1    Dec. 10, 2020

Related U.S. Application Data

(63) Continuation-in-part of application No. PCT/US2018/049609, filed on Sep. 5, 2018.

(60) Provisional application No. 62/554,428, filed on Sep. 5, 2017.

(51) Int. Cl.
| | |
|---|---|
| *C12P 7/24* | (2006.01) |
| *C12N 1/20* | (2006.01) |
| *C12P 5/02* | (2006.01) |

(52) U.S. Cl.
CPC ............... *C12P 7/24* (2013.01); *C12N 1/20* (2013.01); *C12P 5/023* (2013.01)

(58) Field of Classification Search
CPC ........... C12N 1/20; C12N 15/52; Y02E 50/30; C12P 17/06; C12P 7/24; C12P 5/023
See application file for complete search history.

(56) References Cited

U.S. PATENT DOCUMENTS 10,119,145 B2 * 11/2018 Gramajo ............... C12P 7/6436
10,167,482 B2 *  1/2019 Coffin ................. C12N 15/8271
11,008,597 B2 *  5/2021 Del Cardayre ........... C12P 7/42
2012/0122180 A1   5/2012 Austin et al.
2017/0029854 A1   2/2017 Del Cardayre et al.

FOREIGN PATENT DOCUMENTS

WO    2015/157719 A1    10/2015

OTHER PUBLICATIONS

Beld et al., Versatility of acyl-acyl carrier protein synthetases. Chem Biol., 2014, vol. 21(10): 1293-1299. (Year: 2014).*
Zhou et al., A Polyketide Macrolactone Synthase from the Filamentous Fungus *Gibberella zeae*. PNAS., 2008, vol. 105(17): 6249-6254. (Year: 2008).*
Arora et al., Mechanistic and functional insights into fatty acid activation in *Mycobacterium tuberculosis*. Nature Chem. Biol., 2009, vol. 5(3): 166-173 (Year: 2009).*
Barajas et al., Engineered polyketides: Synergy between protein and host level engineering. Synth. Systems Biol., 2017, vol. 2: 147-166. (Year: 2017).*
Dong et al., Characterization of two long-chain fatty acid CoA ligases in the Gram-positive bacterium *Geobacillus hermodenitrificans* NG80-2 Microbiol. Res., 2012, vol. 167: 602-607. (Year: 2012).*
Kim et al., "Two different polyketide synthase genes are required for synthesis of zearalenone in Gibberella zeae." Mol Microbiol. 58(4):1102-1113. (2005).
Mohanty et al., "Fatty Acyl-AMP Ligases and Polyketide Synthases are Unique Enzymes of Lipid Biosynthetic Machinery in *Mycobacterium tuberculosis*." Tuberculosis 91: 448-455 (2011).
GenBank acession No. ABG37977.1 "acyl-acyl carrier protein synthetase"Vibrio harveyi], Jul. 14, 2016 Retrieved from the internet: </www.ncbi.nlm.nih.gov/protein/ABG37977>.
International Search Report and Written Opinion issued for PCT/US18/49609, dated Feb. 5, 2019.

* cited by examiner

*Primary Examiner* — Ganapathirama Raghu
(74) *Attorney, Agent, or Firm* — Lawrence Berkeley National Laboratory; Robin C. Chiang

(57) ABSTRACT

This present invention provides for a genetically modified host cell, or a cell-free reaction system, and related methods and materials for the biocatalytic production of an alkyl lactones from a hydroxy fatty acid, or natural alkyl lactones and esters from sugars using non-natural combinations of enzymes.

14 Claims, 10 Drawing Sheets
Specification includes a Sequence Listing.

AAS: R2 = type II acyl carrier protein
FAAL: R2 = type I acyl carrier protein
FACL: R2 = coenzyme A or N-acetyl cysteamine

SEQUENCE LISTING

```
<160> NUMBER OF SEQ ID NOS: 6

<210> SEQ ID NO 1
<211> LENGTH: 533
<212> TYPE: PRT
<213> ORGANISM: Vibrio harveyi

<400> SEQUENCE: 1
```

Met Asn Gln Tyr Val Asn Asp Pro Ser Asn Tyr Gln Leu Leu Ile Lys
1               5                   10                  15

Asn Leu Leu Phe Ser Pro Val Ala Phe Asn Pro Glu Gln Glu Ile Val
            20                  25                  30

Tyr Ala Asn His Arg Arg His Ser Tyr Lys Thr Phe His Asp Arg Val
        35                  40                  45

Arg Gln Phe Ala Asn Ala Leu Thr Lys Met Gly Val Lys Lys Gly Asp
    50                  55                  60

Thr Val Ala Val Met Asp Tyr Asp Ser His Arg Tyr Leu Glu Cys Tyr
65                  70                  75                  80

Phe Ala Ile Pro Met Ile Gly Ala Lys Leu His Met Ile Asn Val Arg
                85                  90                  95

Leu Ser Pro Glu Gln Ile Leu Tyr Thr Ile Asp His Ala Glu Asp Asp
            100                 105                 110

Ile Ile Leu Ile His Glu Glu Phe Leu Pro Ile Leu Asp Gln Ile Lys
        115                 120                 125

Gly Arg Ile Asp Thr Val Thr Arg Tyr Val Val Leu Arg Asp Asp Glu

```
            130                 135                 140
Glu Cys Glu Tyr Glu Arg Leu Leu Glu Gln Glu Ser Thr Glu Tyr Asn
145                 150                 155                 160

Phe Pro Asp Phe Asp Glu Asn Thr Val Ala Thr Thr Phe Tyr Thr Thr
                165                 170                 175

Gly Thr Thr Gly Phe Pro Lys Gly Val Phe Phe Thr His Arg Gln Leu
            180                 185                 190

Val Leu His Thr Met Gly Ile Leu Ser Thr Ile Gly Thr Asn Ala Ser
        195                 200                 205

Gln Gly Arg Leu His Gln Gly Asp Ile Tyr Met Pro Ile Thr Pro Met
    210                 215                 220

Phe His Val His Ala Trp Gly Leu Pro Tyr Met Ala Thr Met Leu Gly
225                 230                 235                 240

Val Lys Gln Val Tyr Pro Gly Lys Tyr Val Pro Asp Val Leu Leu Asn
                245                 250                 255

Leu Ile Glu Gln Glu Lys Val Thr Phe Ser His Cys Val Pro Thr Ile
            260                 265                 270

Leu His Leu Leu Leu Ser Ser Pro Lys Ser Lys Ala Met Asp Phe Ser
        275                 280                 285

Gly Trp Lys Val Val Ile Gly Ala Ala Leu Pro Lys Ala Leu Cys
    290                 295                 300

Lys Ser Ala Leu Glu Arg Asp Ile Asp Val Phe Ala Gly Tyr Gly Met
305                 310                 315                 320

Ser Glu Thr Gly Pro Ile Leu Ser Ile Val Gln Leu Thr Pro Glu Gln
                325                 330                 335

Leu Glu Leu Asp Val Asp Gln Gln Ala Glu Tyr Arg Ser Lys Thr Gly
            340                 345                 350

Lys Lys Val Ala Leu Val Glu Ala Tyr Ile Val Asp Glu Asp Met Asn
        355                 360                 365

Lys Leu Pro His Asp Gly Glu Thr Ala Gly Glu Ile Val Val Arg Ala
    370                 375                 380

Pro Trp Leu Thr Pro Asn Tyr Tyr Lys Asp Asn Lys Asn Ser Lys Ala
385                 390                 395                 400

Leu Trp Arg Gly Gly Tyr Leu His Thr Gly Asp Val Ala His Ile Asp
                405                 410                 415

Asp Glu Gly Phe Ile Lys Ile Thr Asp Arg Val Lys Asp Met Ile Lys
            420                 425                 430

Ile Ser Gly Glu Trp Val Ser Ser Leu Glu Leu Glu Asp Ile Leu His
        435                 440                 445

Gln His Gln Ser Val Ser Glu Val Ala Val Ile Gly Met Pro His Asn
    450                 455                 460

Lys Trp Gly Glu Val Pro Leu Ala Leu Val Thr Leu Lys Glu Asp Ala
465                 470                 475                 480

Gln Val Thr Glu Lys Glu Leu Leu Gly Phe Ala Lys Asp Phe Ile Asn
                485                 490                 495

Lys Gly Ile Leu Ala Arg Glu Ala Leu Leu Leu Lys Val Lys Ile Val
            500                 505                 510

Asp Glu Ile Ala Lys Thr Ser Val Gly Lys Val Asp Lys Lys Glu Leu
        515                 520                 525

Arg Lys Leu His Leu
    530

<210> SEQ ID NO 2
```

<211> LENGTH: 431
<212> TYPE: PRT
<213> ORGANISM: Artificial Sequence
<220> FEATURE:
<223> OTHER INFORMATION: acpP-zeaTE chimeric enzyme

<400> SEQUENCE: 2

```
Met Ser Thr Ile Glu Glu Arg Val Lys Lys Ile Ile Gly Glu Gln Leu
1               5                   10                  15

Gly Val Lys Gln Glu Val Thr Asn Asn Ala Ser Phe Val Glu Asp
            20                  25                  30

Leu Gly Ala Asp Ser Leu Asp Thr Val Glu Leu Val Met Ala Leu Glu
        35                  40                  45

Glu Glu Phe Asp Thr Glu Ile Pro Asp Glu Glu Ala Glu Lys Ile Thr
    50                  55                  60

Thr Val Gln Ala Ala Ile Asp Tyr Pro Ala Ile Gly Asp Leu Arg Arg
65                  70                  75                  80

Val Phe Ala Pro Lys Ser Thr His Ile Ser Leu Asp Asn Asp Leu Ser
                85                  90                  95

Arg Pro Ser Leu Val Asp Asp Thr Ser Gln Ala Leu Gln Ser Ser Gly
            100                 105                 110

Ser Glu Ser Phe Asp Gln Pro Pro Thr Ser Val Thr Ser Thr Ser Asp
        115                 120                 125

Ser Gly Ser Ile Val Lys Ile Asp Leu Gly Pro Asp Val Asp Ser Pro
130                 135                 140

Ala Pro Lys Ile Lys Ile Thr Leu Leu Gln Gly Arg Pro Gly Asn Gly
145                 150                 155                 160

Arg Thr Pro Phe Tyr Leu Ile Ala Asp Gly Thr Gly Thr Ile Ala Thr
                165                 170                 175

Tyr Ile His Leu Pro Gln Phe Lys Ser Gln Ile Pro Ile Tyr Gly Ile
            180                 185                 190

Asp Ser Pro Phe Leu Arg Cys Pro Thr Arg Phe Thr Thr Asp Val Gly
        195                 200                 205

Ile Thr Gly Ala Ala Arg Phe Ile Thr Glu Ala Leu Met Lys Ala Gln
210                 215                 220

Pro Glu Gly Thr Phe Val Leu Gly Gly Phe Ser Gly Gly Ala Met Leu
225                 230                 235                 240

Ala Tyr Glu Val Cys Arg Gln Leu Ala Ala Asn Arg Lys Val Asp
                245                 250                 255

Ser Leu Met Leu Ile Asp Met Cys Ser Pro Arg Ser Lys Thr Val Glu
            260                 265                 270

Asp Lys Asn Asp Ile Gly Trp Ala Ile Phe Glu Ser Ile Ser Arg Gln
        275                 280                 285

Asn Gly Leu Trp Arg Ser Thr Asp Met Thr Arg Gln His Leu Gln Ala
    290                 295                 300

Ile Phe Ala Ala Val Ala Thr Tyr His Pro Gln Pro Leu Lys Ala Ser
305                 310                 315                 320

Glu Arg Pro Lys Arg Thr Ala Ile Ile Trp Ala Glu Lys Gly Met Ile
                325                 330                 335

Asp Arg Cys Ala Gly Asp Ser Glu Leu Met Gln Lys Leu Ala Lys Arg
            340                 345                 350

Gly Ile Pro Thr Glu Pro Tyr Pro Lys Phe Met Glu Asp Ser Glu Leu
        355                 360                 365

Gly Pro Val Ala Trp Gly Leu Pro His Lys Thr Lys Asn Asp Leu Gly
    370                 375                 380
```

```
Pro Asn Gly Trp Glu Arg Tyr Val Gly Asp Ala Leu Cys Leu Ser Met
385                 390                 395                 400

Pro Ala Asp His Leu Glu Met Pro Met Pro Gly His Val His Leu Leu
            405                 410                 415

His Glu Lys Met Thr Arg Ala Phe Glu Phe Phe Asn Glu Ala Gly
            420                 425                 430

<210> SEQ ID NO 3
<211> LENGTH: 2080
<212> TYPE: PRT
<213> ORGANISM: Artificial Sequence
<220> FEATURE:
<223> OTHER INFORMATION: lipLM-ppsA chimeric enzyme

<400> SEQUENCE: 3

Met Ser Glu His Arg Gly Ser Ala Gly Gly Ser Val Leu Phe Pro Arg
1               5                   10                  15

Thr Gly Thr Val Leu Pro Trp Val Leu Thr Gly Pro Gly Ala Ala Ala
                20                  25                  30

Val Arg Ala Arg Ser Glu Ala Leu Arg Thr His Leu Arg Ala Ser Thr
            35                  40                  45

Glu Trp Ser Pro Ala Gly Val Gly Gln Ala Leu Leu Ala Gly Thr Gly
    50                  55                  60

Ala Gly Ala Asp Thr His Arg Ala Val Val Leu Ala Gly Asp Arg Ala
65                  70                  75                  80

Gln Thr Leu Asn Ala Leu Ala Ala Leu Ser Ala Gly Ala Asp His Pro
                85                  90                  95

Ala Val Phe Thr Ser Thr Arg Ala Asp Ala Ser Pro Ala Gly Pro Val
            100                 105                 110

Phe Val Phe Pro Gly Gln Gly Ser Gln Trp Thr Gly Met Ala Arg Glu
        115                 120                 125

Leu Leu Asp Ser Ala Pro Val Phe Ala Arg Lys Leu His Asp Cys Ala
    130                 135                 140

Asp Ala Phe Ala Pro Tyr Leu Gly His Ser Leu Leu Asp Ser Val Thr
145                 150                 155                 160

Gly Ala Ala Gly Gly Pro Glu Pro Val Gly Ala Asp Val Val Gln Pro
                165                 170                 175

Ala Leu Phe Ala Val Met Val Ala Leu Thr Asp Leu Trp Asn Ala Ala
            180                 185                 190

Gly Val Ala Pro Gly Ala Leu Leu Gly His Ser Leu Gly Glu Leu Ala
        195                 200                 205

Ala Ala His Val Ala Gly Val Leu Ser Leu Asp Asp Ser Ala Arg Val
    210                 215                 220

Val Ala Arg Trp Ser Gln Ala Gln Ala Thr Leu Ala Gly Arg Gly Asp
225                 230                 235                 240

Met Val Ser Val Leu Leu Pro Ala Asp Glu Leu Ala Asp Leu Asp
                245                 250                 255

Arg Arg Trp Pro Gly Arg Leu Val Val Ala Val Glu Asn Gly Pro Gly
                260                 265                 270

Ser Ala Val Ala Ser Gly Asp Leu Asp Ala Ala Glu Leu Val Ala
            275                 280                 285

His Leu Thr Ala Glu Gly Ile His Ala Arg Arg Val Asp Val Gly Leu
    290                 295                 300

Ala Ala His Ser Pro His Ile Asp Ala Ile Leu Pro Arg Ile Arg Ala
305                 310                 315                 320
```

```
Asp Ile Ala Pro Ile Arg Ala His Thr Pro Ser Ile Pro Val Tyr Ser
                325                 330                 335

Ala Leu His Gly Gly Ala Leu Asp Gly Thr Pro Met Asp Ala Ala Tyr
            340                 345                 350

Trp Cys Arg Asn Leu Arg Ser Thr Val Arg Phe Ala Asp Ala Thr Arg
        355                 360                 365

Ala Ala Leu Glu Ala Gly His Thr Thr Phe Val Glu Val Ser Pro His
370                 375                 380

Pro Val Leu Thr Thr Ala Met Glu Val Ser Ala Thr Arg Ala Ala His
385                 390                 395                 400

Ala Ala Thr Val Leu Gly Thr Leu Arg Arg Gly Glu Gly Gly Pro Ser
                405                 410                 415

Arg Phe Leu Ala Ser Leu Ala Glu Leu His Val Ser Gly Gly Asp Ala
            420                 425                 430

Asp Leu Arg Thr Val Leu Pro Ala Ser Gln Ala Ala Gly Leu Pro Glu
        435                 440                 445

Thr Val Leu Thr Ala Gly Pro Arg Gly Glu Ser Ala Asp Gly Asp Ser
450                 455                 460

Arg His Glu Val Leu Cys Ala Arg Leu Ala Pro Leu Asp Pro Ala Glu
465                 470                 475                 480

Arg Arg Ala Gln Leu Leu Thr Val Val Arg Glu Ser Ala Ala Ala Ala
                485                 490                 495

Leu Asp Gly Asp Asp Gln Gly Ser Ile Asp Gly Arg Arg Thr Phe Arg
            500                 505                 510

Asp Leu Gly Ile Thr Ser Leu Ala Val Gly Ile Arg Asp Arg Leu
        515                 520                 525

His Ser Ala Thr Gly Leu Arg Leu Ser Pro Thr Val Val Phe Asp His
530                 535                 540

Pro Thr Pro Asp Ala Leu Ala Ala His Leu Asp Thr Glu Leu Phe Gly
545                 550                 555                 560

Thr Gly Ala Asp Ala Glu Pro Ala Pro Ala Ala Gly Gly Arg Ala Val
                565                 570                 575

Pro His Asp Glu Pro Ile Ala Val Val Gly Met Gly Cys Arg Phe Pro
            580                 585                 590

Gly Gly Ile Ser Gly Pro Glu Ala Leu Trp Gln Phe Leu Cys Asp Arg
        595                 600                 605

Lys Ser Ser Ile Gly Arg Val Pro Asp Glu Arg Trp Ala Gln Phe Asp
610                 615                 620

Asp Gly Ser Pro Ala Val Lys Ala Leu Leu Ala Arg Thr Thr Arg Trp
625                 630                 635                 640

Gly Ser Tyr Leu Thr Asp Ile Asp Ala Phe Asp Ala Asp Phe Phe Glu
                645                 650                 655

Ile Ser Ala Ser Glu Ala Asp Lys Met Asp Pro Gln Gln Arg Leu Leu
            660                 665                 670

Leu Glu Val Ala Trp Glu Ala Leu Glu His Ala Gly Ile Pro Pro Ser
        675                 680                 685

Ser Leu Arg Arg Ser Gln Thr Gly Val Phe Ala Gly Ser Cys Leu Ser
690                 695                 700

Glu Tyr Gly Ala Ile Ala Ser Thr Asp Leu Thr Gln Val Asp Gly Trp
705                 710                 715                 720

Ser Asn Thr Gly Gly Ala Met Ser Ile Ile Ala Asn Arg Leu Ser Tyr
                725                 730                 735
```

-continued

Phe Leu Asp Leu Arg Gly Pro Ser Val Ala Val Asp Thr Ala Cys Ser
                740                 745                 750

Ser Ser Leu Val Ala Ile His Leu Ala Cys Gln Ser Leu Arg Met Gln
        755                 760                 765

Asp Ser Asn Leu Ala Ile Ala Ala Gly Val Asn Leu Leu Ser Pro
    770                 775                 780

Ala Val Phe Arg Gly Phe Asp Gln Val Gly Ala Leu Ser Pro Thr Gly
785                 790                 795                 800

Asn Cys Arg Ala Phe Asp Ala Ala Asp Gly Phe Val Arg Gly Glu
                805                 810                 815

Gly Ala Gly Val Val Leu Lys Arg Leu Thr Asp Ala Gln Gln Asp
            820                 825                 830

Gly Asp Arg Val Leu Ala Val Ile Cys Gly Ser Ala Ile Asn Gln Asp
            835                 840                 845

Gly Arg Ser Asn Gly Leu Met Ala Pro Asn Pro Ala Ala Gln Gln Ala
            850                 855                 860

Val Leu Arg Ala Ala Tyr Thr Asn Ala Gly Met Gln Pro Ser Glu Val
865                 870                 875                 880

Asp Tyr Val Glu Ala His Gly Thr Gly Thr Leu Leu Gly Asp Pro Ile
                885                 890                 895

Glu Ala Arg Ala Leu Gly Ser Val Leu Gly Arg Gly Arg Pro Glu Glu
            900                 905                 910

Ser Pro Leu Leu Ile Gly Ala Val Lys Thr Asn Leu Gly His Thr Glu
        915                 920                 925

Ala Ala Ala Gly Ile Ala Gly Phe Ile Lys Ala Val Leu Ala Val Gln
        930                 935                 940

His Gly Arg Ile Pro Pro Asn Gln Arg Phe Glu Ser Pro Asn Pro His
945                 950                 955                 960

Ile Ala Phe Ala Asp Leu Arg Met Lys Val Val Asp Glu Leu Thr Asp
                965                 970                 975

Trp Pro Asp Thr Gly His Pro Arg Arg Ala Gly Val Ser Phe Gly
                980                 985                 990

Phe Gly Gly Thr Asn Ala His Val  Val Ile Glu Gln Gly  Gln Glu Ala
        995                 1000                1005

Ala Ser  Ser Pro Glu Ala Gly  Leu Thr Pro Ala Leu  Ser Thr Leu
    1010                1015                1020

Val Val  Ala Gly Lys Thr Pro  Ala Arg Val Ala Ala  Thr Ala Gly
    1025                1030                1035

Met Leu  Ala Asp Trp Met Glu  Gly Pro Gly Ala Glu  Val Ala Leu
    1040                1045                1050

Ala Asp  Val Ala His Thr Leu  Asn His His Arg Ser  Arg Gln Ala
    1055                1060                1065

Arg Phe  Gly Thr Val Val Ala  Arg Glu Arg Ala Gln  Ala Val Ala
    1070                1075                1080

Gly Leu  Arg Ala Leu Ala Ala  Asn Gln His Ala Pro  Gly Val Val
    1085                1090                1095

Asn Pro  Ala Asp Ala Pro Pro  Glu Pro Gly Thr Val  Phe Val Tyr
    1100                1105                1110

Ser Gly  Arg Gly Ser Gln Trp  Ala Gly Met Gly Arg  Gln Leu Leu
    1115                1120                1125

Ala Asp  Glu Pro Val Phe Ala  Ala Val Ala Glu  Leu Glu Pro
    1130                1135                1140

Val Phe  Leu Ala Glu Ala Gly  Phe Ser Leu His Asp  Val Leu Ala

-continued

|  | 1145 |  |  | 1150 |  |  | 1155 |  |
| --- | --- | --- | --- | --- | --- | --- | --- | --- |

Asn Gly Thr Glu Leu Val Gly Ile Glu Gln Ile Gln Leu Gly Leu
              1160                1165             1170

Ile Gly Met Gln Leu Thr Leu Thr Glu Leu Trp Arg Ser Tyr Gly
    1175                1180                1185

Ile Gln Pro Asp Leu Val Ile Gly His Ser Met Gly Glu Val Ala
    1190                1195                1200

Ala Ala Val Val Ala Gly Ala Leu Thr Pro Ala Glu Gly Leu Arg
    1205                1210                1215

Val Thr Ala Val Arg Ser Arg Leu Met Ala Pro Leu Ser Gly Gln
    1220                1225                1230

Gly Gly Met Ala Leu Leu Glu Leu Asp Ala Ser Gln Thr Glu Ala
    1235                1240                1245

Leu Ile Ala Asp Tyr Pro Gln Val Thr Leu Gly Ile Tyr Asn Ser
    1250                1255                1260

Pro Arg Gln Thr Val Ile Ser Gly Pro Thr Asp Gln Ile Asp Glu
    1265                1270                1275

Leu Ile Thr Val Val Arg Ala Arg Asp Arg Phe Ala Thr Arg Val
    1280                1285                1290

Asn Ile Glu Val Ala Pro His Asn Pro Ala Met Asp Ala Leu Gln
    1295                1300                1305

Pro Gln Met Arg Ser Glu Leu Ala Asp Leu Ala Pro Arg Thr Pro
    1310                1315                1320

Thr Ile Pro Ile Ile Ser Thr Thr Tyr Ala Asp Leu Gly Ser Ala
    1325                1330                1335

Arg Glu Ser Gly Pro Thr Phe Asp Ala Glu His Trp Ala Ile Asn
    1340                1345                1350

Met Arg Asn Pro Val His Phe Gln Gln Ala Ile Thr Ala Ala Ala
    1355                1360                1365

Thr Asp Lys His Asn Phe Ile Glu Ile Ser Ala His Pro Leu Leu
    1370                1375                1380

Thr Gln Ala Ile Leu Glu Thr Leu His Thr Val Gln Pro Gly Ser
    1385                1390                1395

Lys Tyr Thr Ser Leu Gly Thr Leu Gln Arg Asp Ser Asp Asp Thr
    1400                1405                1410

Ile Val Phe Arg Thr Asn Leu Asn Thr Val Arg Thr Ala Pro Pro
    1415                1420                1425

Gln Thr Pro His Pro Pro Glu Pro His Pro Gln Ile Pro Thr Thr
    1430                1435                1440

Pro Trp His His Thr His His Trp Ile Asp Thr Pro Ala Val Ala
    1445                1450                1455

Ser Arg Ser Ala Ser Thr Pro Asp Lys Asp Ala Ala Gly Ser Ser
    1460                1465                1470

Glu Pro Ser Val Ser Gly Asp Ser Asp Asp Ala Val Asp Ser Cys
    1475                1480                1485

His Tyr Arg Val Gly Trp Pro Thr Lys Pro Leu Ala Asp Ala Lys
    1490                1495                1500

Ala Ser Thr Glu Thr Ala Ser Gly Thr Arg Trp Leu Val Phe Ala
    1505                1510                1515

Asp Ala Glu Leu Gly Ala Glu Leu Gly Leu Ala Ala Gly Ala Gln
    1520                1525                1530

Thr Arg Val Asp Val Ile Asp Pro Ser Ala Leu Thr Glu Glu Ser
    1535                1540                1545

```
Glu Leu Leu Ala Ala Leu Ala Gly Val Glu His Val Val Tyr Ala
1550                1555                1560

Pro Pro Ala Gly Lys Ser Leu Asp Val Asn Ala Ala Tyr Gln Leu
1565                1570                1575

Phe His Gln Val Arg Arg Leu Val Thr Val Met Thr Lys Ala Ser
1580                1585                1590

Leu Thr Ala Lys Leu Leu Leu Val Thr Arg Asn Ala Gln Pro Ile
1595                1600                1605

Ala Glu Gly Asp Arg Ala Asn Pro Ala His Gly Val Leu Trp Gly
1610                1615                1620

Leu Gly Arg Thr Ile Ala Leu Glu His Pro Glu Ile Trp Arg Gly
1625                1630                1635

Ile Ile Asp Leu Asp Glu Ser Met Pro Ala Glu Leu Ala Ala Pro
1640                1645                1650

Lys Ile Leu Gly Glu Val Thr Gly Thr Asp Gly Glu Asp Gln Val
1655                1660                1665

Val Tyr Arg Cys Gly Gly Arg His Val Pro Arg Leu Gln Arg Arg
1670                1675                1680

Thr Ala Pro Ala Val Ala Pro Val Thr Leu Asp Pro Asn Ser Ser
1685                1690                1695

Gln Leu Val Ile Gly Ala Thr Gly Asn Ile Gly Pro Tyr Leu Ile
1700                1705                1710

Arg Gln Leu Ala Gln Met Gly Ala Lys Thr Val Val Ala Val Ser
1715                1720                1725

Arg Asn Pro Gly Gln Arg Leu Gln Glu Leu Ala Glu Ser Leu Ala
1730                1735                1740

Ala Glu Gly Thr Asn Leu Val Ile Glu Ala Ala Asp Ala Thr Asp
1745                1750                1755

Glu Ala Ala Met Thr Ala Leu Phe Asp Arg Phe Gly Ala Asp Leu
1760                1765                1770

Pro Pro Leu Glu Gly Ile Tyr Leu Ala Ala Phe Ala Gly Gly Pro
1775                1780                1785

Val Leu Leu Asn Glu Met Thr Asp Ala Asp Val Arg Ala Met Phe
1790                1795                1800

Ala Pro Lys Leu Asp Ala Ala Leu Leu His Arg Leu Ser Leu
1805                1810                1815

Lys Val Pro Ala Arg His Phe Val Leu Phe Ser Ser Ile Ser Gly
1820                1825                1830

Leu Ile Gly Ser Arg Trp Leu Ala His Tyr Thr Ala Thr Ser Gly
1835                1840                1845

Tyr Leu Asp Ala Leu Ala Tyr Ala Arg His Ala Leu Gly Leu Pro
1850                1855                1860

Ala Thr Thr Val Asn Trp Gly Leu Trp Lys Ser Leu Ala Asp Ala
1865                1870                1875

Glu His Asp Ala Ser Gln Val Ser Val Gly Ser Gly Leu Leu Pro
1880                1885                1890

Met Gln Asp Glu Val Ala Ile Gly Thr Leu Pro Leu Leu Met Asn
1895                1900                1905

Pro Ala Ala Gly Val His Ser Val Val Val Glu Ala Asp Trp Pro
1910                1915                1920

Leu Leu Ala Ala Ala Tyr Arg Thr Arg Gly Ser Leu His Ile Val
1925                1930                1935
```

```
Asp Asp Leu Leu Arg Asp Phe Ala Glu Ala Ser Thr Ile Pro Ala
    1940                1945                1950

Arg Asp Trp Ser His Leu Ser Ala Gln Glu Val Arg Thr Glu Phe
    1955                1960                1965

Glu Ala Gly Leu Arg Arg Ile Val Ala Arg Glu Leu Arg Val Ser
    1970                1975                1980

Glu Ser Asp Leu Glu Thr Asp Arg Pro Leu Ala Glu Leu Gly Leu
    1985                1990                1995

Asn Ser Leu Met Ala Met Ala Ile Arg Arg Glu Ala Glu Met Phe
    2000                2005                2010

Val Gly Ile Glu Leu Ser Ala Thr Met Leu Phe Asn His Pro Thr
    2015                2020                2025

Val Ala Ser Leu Ala Ser Tyr Leu Ala Asn Arg Val Ala Pro Gln
    2030                2035                2040

Asp Asn Ser Ser Asn Asp Gln Met Ala Glu Leu Ser Ala Ser Ala
    2045                2050                2055

Gly Ser Thr Leu Asp Ser Leu Phe Asp Arg Ile Glu Ser Ser Ser
    2060                2065                2070

Leu Leu Pro Glu Gly Pro Gly
    2075                2080

<210> SEQ ID NO 4
<211> LENGTH: 2071
<212> TYPE: PRT
<213> ORGANISM: Artificial Sequence
<220> FEATURE:
<223> OTHER INFORMATION: lipLM-ppsB chimeric enzyme

<400> SEQUENCE: 4

Met Ser Glu His Arg Gly Ser Ala Gly Gly Ser Val Leu Phe Pro Arg
1               5                   10                  15

Thr Gly Thr Val Leu Pro Trp Val Leu Thr Gly Pro Gly Ala Ala Ala
                20                  25                  30

Val Arg Ala Arg Ser Glu Ala Leu Arg Thr His Leu Arg Ala Ser Thr
            35                  40                  45

Glu Trp Ser Pro Ala Gly Val Gly Gln Ala Leu Leu Ala Gly Thr Gly
    50                  55                  60

Ala Gly Ala Asp Thr His Arg Ala Val Val Leu Ala Gly Asp Arg Ala
65                  70                  75                  80

Gln Thr Leu Asn Ala Leu Ala Ala Leu Ser Ala Gly Ala Asp His Pro
                85                  90                  95

Ala Val Phe Thr Ser Thr Arg Ala Asp Ala Ser Pro Ala Gly Pro Val
            100                 105                 110

Phe Val Phe Pro Gly Gln Gly Ser Gln Trp Thr Gly Met Ala Arg Glu
        115                 120                 125

Leu Leu Asp Ser Ala Pro Val Phe Ala Arg Lys Leu His Asp Cys Ala
    130                 135                 140

Asp Ala Phe Ala Pro Tyr Leu Gly His Ser Leu Leu Asp Ser Val Thr
145                 150                 155                 160

Gly Ala Ala Gly Gly Pro Glu Pro Val Gly Ala Asp Val Val Gln Pro
                165                 170                 175

Ala Leu Phe Ala Val Met Val Ala Leu Thr Asp Leu Trp Asn Ala Ala
            180                 185                 190

Gly Val Ala Pro Gly Ala Leu Leu Gly His Ser Leu Gly Glu Leu Ala
        195                 200                 205
```

-continued

```
Ala Ala His Val Ala Gly Val Leu Ser Leu Asp Asp Ser Ala Arg Val
210                 215                 220

Val Ala Arg Trp Ser Gln Ala Gln Ala Thr Leu Ala Gly Arg Gly Asp
225                 230                 235                 240

Met Val Ser Val Leu Leu Pro Ala Asp Glu Leu Ala Asp Leu Leu Asp
                245                 250                 255

Arg Arg Trp Pro Gly Arg Leu Val Val Ala Val Glu Asn Gly Pro Gly
            260                 265                 270

Ser Ala Val Ala Ser Gly Asp Leu Asp Ala Ala Ala Glu Leu Val Ala
        275                 280                 285

His Leu Thr Ala Glu Gly Ile His Ala Arg Arg Val Asp Val Gly Leu
290                 295                 300

Ala Ala His Ser Pro His Ile Asp Ala Ile Leu Pro Arg Ile Arg Ala
305                 310                 315                 320

Asp Ile Ala Pro Ile Arg Ala His Thr Pro Ser Ile Pro Val Tyr Ser
                325                 330                 335

Ala Leu His Gly Gly Ala Leu Asp Gly Thr Pro Met Asp Ala Ala Tyr
            340                 345                 350

Trp Cys Arg Asn Leu Arg Ser Thr Val Arg Phe Ala Asp Ala Thr Arg
        355                 360                 365

Ala Ala Leu Glu Ala Gly His Thr Thr Phe Val Glu Val Ser Pro His
370                 375                 380

Pro Val Leu Thr Thr Ala Met Glu Val Ser Ala Thr Arg Ala Ala His
385                 390                 395                 400

Ala Ala Thr Val Leu Gly Thr Leu Arg Arg Gly Glu Gly Gly Pro Ser
                405                 410                 415

Arg Phe Leu Ala Ser Leu Ala Glu Leu His Val Ser Gly Gly Asp Ala
            420                 425                 430

Asp Leu Arg Thr Val Leu Pro Ala Ser Gln Ala Ala Gly Leu Pro Glu
        435                 440                 445

Thr Val Leu Thr Ala Gly Pro Arg Gly Glu Ser Ala Asp Gly Asp Ser
450                 455                 460

Arg His Glu Val Leu Cys Ala Arg Leu Ala Pro Leu Asp Pro Ala Glu
465                 470                 475                 480

Arg Arg Ala Gln Leu Leu Thr Val Val Arg Glu Ser Ala Ala Ala Ala
                485                 490                 495

Leu Asp Gly Asp Asp Gln Gly Ser Ile Asp Gly Arg Arg Thr Phe Arg
            500                 505                 510

Asp Leu Gly Ile Thr Ser Leu Ala Ala Val Gly Ile Arg Asp Arg Leu
        515                 520                 525

His Ser Ala Thr Gly Leu Arg Leu Ser Pro Thr Val Val Phe Asp His
530                 535                 540

Pro Thr Pro Asp Ala Leu Ala Ala His Leu Asp Thr Glu Leu Phe Gly
545                 550                 555                 560

Thr Gly Ala Asp Ala Glu Pro Ala Pro Ala Ala Gly Gly Arg Ala Val
                565                 570                 575

Pro His Asp Glu Pro Val Ala Val Val Gly Ile Gly Cys Arg Phe Pro
            580                 585                 590

Gly Asn Val Thr Gly Pro Asp Ser Phe Trp Asp Leu Leu Val Glu Gly
        595                 600                 605

Gly Asn Ala Ile Ser Gly Ile Pro Ala Glu Arg Trp Asp Ala Asp Asp
610                 615                 620

Tyr Tyr His Pro Asp Pro Leu Thr Pro Gly His Met Thr Thr Lys Trp
```

-continued

```
            625                 630                 635                 640
Gly Ala Phe Val Ala Asp Ile Ala Gly Phe Asp Ala Glu Phe Phe Gly
                    645                 650                 655
Ile Thr Pro Arg Glu Ala Ala Ser Met Asp Pro Gln Gln Arg Met Leu
                660                 665                 670
Leu Glu Val Thr Trp Glu Ala Leu Glu His Ala Gly Ile Pro Thr Glu
            675                 680                 685
Ser Leu Ala Gly Thr Arg Thr Ala Val Met Met Gly Val Tyr Phe Asn
        690                 695                 700
Glu Tyr Gln Ser Met Leu Ala Ser Ser Arg Glu Asn Val Asp Ala Tyr
705                 710                 715                 720
Thr Gly Thr Gly Asn Ser His Ser Ile Thr Ala Gly Arg Ile Ser Tyr
                    725                 730                 735
Leu Leu Gly Leu Arg Gly Pro Ala Ala Ile Asp Thr Ala Cys Ser
                740                 745                 750
Ser Ser Leu Ser Ala Ile His Leu Ala Cys Gln Ser Leu Arg Leu Arg
            755                 760                 765
Glu Thr Asp Leu Ala Leu Ala Gly Gly Val Ser Ala Thr Leu Arg Pro
        770                 775                 780
Glu Thr Gln Ile Ala Ile Ser Ala Trp Gly Leu Leu Ser Pro Glu Gly
785                 790                 795                 800
Arg Cys Ala Thr Phe Asp Ala Ala Asp Gly Phe Val Arg Gly Glu
                    805                 810                 815
Gly Ala Gly Val Val Leu Lys Arg Leu Thr Asp Ala Leu Arg Asp
                820                 825                 830
Gln Asp Gln Ile Leu Ala Val Arg Gly Ser Ala Val Asn Gln Asp
            835                 840                 845
Gly Arg Ser Asn Gly Ile Thr Ala Pro Asn Thr Ala Gln Cys Asp
        850                 855                 860
Val Ile Ala Asp Ala Leu Arg Ser Ala Asp Val Ala Pro Glu Ser Val
865                 870                 875                 880
His Tyr Val Glu Thr His Gly Thr Gly Thr Gln Leu Gly Asp Pro Ile
                    885                 890                 895
Glu Phe Glu Ala Leu Ala Ala Thr Tyr Gly Leu Ile Lys Gly Gln Asp
                900                 905                 910
Gly Asp Ser Cys Ala Leu Gly Ala Val Lys Thr Asn Ile Gly His Leu
            915                 920                 925
Glu Ala Ala Ser Gly Val Ala Gly Phe Ile Lys Ala Val Leu Ala Val
        930                 935                 940
Gln His Gly Gln Ile Pro Pro Asn Leu His Phe Ser Gln Trp Asn Pro
945                 950                 955                 960
Ala Ile Asp Ala Ala Ser Thr Arg Leu Phe Val Pro Leu Asp Asn Ile
                    965                 970                 975
Ala Trp Pro Ser Asp Ser Gly Pro Arg Arg Ala Ala Val Ser Ser Phe
                980                 985                 990
Gly Leu Gly Gly Thr Asn Ala His  Ala Ile Val Glu Gln Gly Pro Glu
            995                 1000                1005
Leu Ser  Pro Ala Gly Arg Arg  Gly Thr Asp Asp Glu  Val Thr Thr
    1010                 1015                1020
Leu Val  Val Ala Gly Lys Thr  Pro Ala Arg Val Ala  Ala Thr Ala
    1025                 1030                1035
Gly Met  Leu Ala Asp Trp Met  Glu Gly Pro Gly Ala  Glu Val Ala
    1040                 1045                1050
```

```
Leu Ala Asp Val Ala His Thr Leu Asn His His Arg Ser Arg Gln
1055                1060                1065

Ala Arg Phe Gly Thr Val Val Ala Arg Glu Arg Ala Gln Ala Val
1070                1075                1080

Ala Gly Leu Arg Ala Leu Ala Ala Asn Gln His Ala Pro Gly Val
1085                1090                1095

Val Asn Pro Ala Asp Ala Pro Pro Glu Pro Gly Thr Val Phe Val
1100                1105                1110

Tyr Ser Gly Arg Gly Ser Gln Trp Ala Gly Met Gly Arg Gln Leu
1115                1120                1125

Leu Ala Asp Glu Pro Ala Phe Ala Ala Ala Val Ala Glu Leu Glu
1130                1135                1140

Pro Val Phe Leu Ala Glu Ala Gly Phe Ser Leu His Asp Val Leu
1145                1150                1155

Ala Asn Gly Thr Glu Leu Val Gly Ile Glu Gln Ile Gln Leu Gly
1160                1165                1170

Leu Ile Gly Met Gln Leu Thr Leu Thr Glu Leu Trp Arg Ser Tyr
1175                1180                1185

Gly Ile Gln Pro Asp Leu Val Ile Gly His Ser Met Gly Glu Val
1190                1195                1200

Ala Ala Ala Val Val Ala Gly Ala Leu Thr Pro Ala Glu Gly Leu
1205                1210                1215

Arg Val Thr Ala Val Arg Ser Arg Leu Met Ala Pro Leu Ser Gly
1220                1225                1230

Gln Gly Gly Met Ala Leu Leu Gly Leu Asp Ala Ser Gln Thr Glu
1235                1240                1245

Ala Leu Ile Ala Asp Tyr Pro Gln Val Thr Leu Gly Ile Tyr Asn
1250                1255                1260

Ser Pro Arg Gln Thr Val Ile Ser Gly Pro Thr Asp Gln Ile Asp
1265                1270                1275

Glu Leu Ile Thr Val Val Arg Ala Arg Asp Arg Phe Ala Thr Arg
1280                1285                1290

Val Asn Ile Glu Val Ala Pro His Asn Pro Ala Met Asp Ala Leu
1295                1300                1305

Gln Pro Gln Met Arg Ser Glu Leu Ala Asp Leu Ala Pro Arg Thr
1310                1315                1320

Pro Thr Ile Pro Ile Ile Ser Thr Thr Tyr Ala Asp Leu Gly Ser
1325                1330                1335

Ala Arg Glu Ser Gly Pro Thr Phe Asp Ala Glu His Trp Ala Ile
1340                1345                1350

Asn Met Arg Asn Pro Val His Phe Gln Gln Ala Ile Thr Ala Ala
1355                1360                1365

Ala Thr Asp Lys His Asn Phe Ile Glu Ile Ser Ala His Pro Leu
1370                1375                1380

Leu Thr Gln Ala Ile Leu Glu Thr Leu His Thr Val Gln Pro Gly
1385                1390                1395

Ser Lys His Thr Cys Leu Gly Thr Leu Gln Arg Asp Ser Asp Asp
1400                1405                1410

Thr Ile Val Phe Arg Thr Asn Leu Asn Thr Val Arg Thr Ala Pro
1415                1420                1425

Pro Gln Thr Pro His Pro Pro Glu Pro His Pro Gln Ile Pro Thr
1430                1435                1440
```

```
Thr Pro Trp His His Thr His His Trp Ile Asp Asn Ala Ala Ser
    1445            1450            1455

Ser Ser Pro Ala Leu Ser Arg Ser Glu Ser Arg Asp Gly Thr Gly
    1460            1465            1470

Ala Ala Leu Asp Thr Arg Trp Ser Pro Glu Ser Gly Ser Leu Leu
    1475            1480            1485

Asp Glu Trp Ser His Lys Val Val Trp Ala Ala Gln Ser Leu Pro
    1490            1495            1500

Asp Thr Pro Ser Ala Gln Thr Ala Val His Gly Arg Trp Leu Val
    1505            1510            1515

Leu Gly Asn Ala Asp Leu Ala Ala Glu Leu Gly Arg Gly Ala Asp
    1520            1525            1530

Val Leu Asp Ser Asp Ser Glu Pro Ala Ala Leu Ala Arg Ala Leu
    1535            1540            1545

Ser Asp Val Asp Tyr Val Leu Tyr Ala Pro Pro Val Pro Ala Asp
    1550            1555            1560

Pro Leu Asp Val Ala Glu Ala Tyr Gln Leu Phe His Gln Ala Arg
    1565            1570            1575

Arg Leu Ala Thr Ala Met Ile Ala Asn Gly Ser Pro Ala Lys Leu
    1580            1585            1590

Leu Ile Ala Thr Arg Asn Ala Gln Pro Ile Ala Glu Gly Asp Pro
    1595            1600            1605

Ala Asn Pro Ser His Gly Val Leu Trp Gly Leu Gly Arg Thr Ile
    1610            1615            1620

Thr Leu Glu His Pro Glu Ile Trp Gly Ala Ile Ile Asp Phe Asp
    1625            1630            1635

Asn Ser Val Pro Ala Gln Val Val Ala Arg Gln Val Leu Asp Glu
    1640            1645            1650

Ala Asp Ala Thr Asp Ser Glu Asp Gln Val Val Tyr Arg Ser Gly
    1655            1660            1665

Val Arg His Val Pro Arg Leu Arg Arg His Ser Leu Ala Ala Gln
    1670            1675            1680

Pro Val Ala Leu Asp Ala Gly Ala Ser Gln Leu Val Ile Gly Ala
    1685            1690            1695

Thr Gly Asn Ile Gly Pro His Leu Ile Asn Gln Leu Ala Glu Met
    1700            1705            1710

Gly Ala Lys Thr Ile Val Ala Val Ser Arg Asn Pro Gly Gln Arg
    1715            1720            1725

Leu Gln Lys Leu Ala Glu Ser Leu Ala Ala Glu Gly Val Asn Leu
    1730            1735            1740

Val Ile Ala Ala Ala Asp Ala Thr Asp Glu Ala Ala Met Thr Ala
    1745            1750            1755

Leu Phe Asp Arg Phe Gly Ala Asp Leu Pro Pro Leu Glu Gly Ile
    1760            1765            1770

Tyr Leu Ala Ala Phe Ala Gly Gln Pro Val Leu Leu Thr Glu Met
    1775            1780            1785

Thr Asn Asp Asp Val Thr Ala Met Phe Ala Pro Lys Leu Asp Ala
    1790            1795            1800

Ala Ala Leu Leu His Arg Leu Ser Leu Lys Val Pro Val Arg His
    1805            1810            1815

Phe Val Leu Phe Ser Ser Ile Ser Gly Leu Ile Gly Ser Arg Trp
    1820            1825            1830

Leu Ala His Tyr Thr Ala Thr Ser Gly Tyr Leu Asp Ala Leu Ala
```

```
               1835                1840                1845

Tyr Ala Arg Arg Val Met Gly Leu Pro Ala Thr Val Asn Trp
        1850                1855                1860

Gly Leu Trp Lys Ser Leu Ala Asp Ala Glu His Asp Ala Ser Gln
1865                1870                1875

Val Ser Leu Gly Ser Gly Leu Val Pro Met Gln Asp Asp Val Ala
    1880                1885                1890

Ile Gly Ala Leu Pro Leu Val Met Ser Gln Ala Ala Gly Val His
    1895                1900                1905

Ser Val Val Val Ala Ala Asp Trp Pro Leu Leu Ala Ala Ala Tyr
    1910                1915                1920

Arg Thr Arg Gly Ser Leu Arg Ile Val Asp Asp Val Leu Pro Val
    1925                1930                1935

Ser Asp Glu Thr Thr Val Leu Glu Ser Glu Phe Arg Val Ala Leu
    1940                1945                1950

Arg Asn Cys Ala Pro Glu Arg Arg His Asp Met Leu His Asp Gln
    1955                1960                1965

Val Ala Met Leu Ala Ala Asn Val Met Gly Leu His Ala Gly Glu
    1970                1975                1980

Ser Leu Asp Pro Ser Thr Gly Phe Phe Gln Leu Gly Met Asp Ser
    1985                1990                1995

Leu Met Ser Val Thr Leu Gln Arg Ala Leu Ser Asp Ser Leu Gly
    2000                2005                2010

Glu Phe Leu Pro Pro Ser Val Phe Asp Tyr Pro Thr Val Tyr
    2015                2020                2025

Ser Leu Thr Asp Tyr Leu Ala Thr Ile Leu Pro Glu Leu Glu Thr
    2030                2035                2040

Asp Asp Glu Ser Thr Ala Asp Val Tyr Asp Glu Leu Thr Glu Ala
    2045                2050                2055

Glu Leu Leu Glu Gln Leu Ser Gln Arg Leu Arg Gly Thr
    2060                2065                2070

<210> SEQ ID NO 5
<211> LENGTH: 2460
<212> TYPE: PRT
<213> ORGANISM: Artificial Sequence
<220> FEATURE:
<223> OTHER INFORMATION: ppsBC-pikTE chimeric enzyme

<400> SEQUENCE: 5

Met Arg Ser Val Tyr Ser Arg Ile Ser Ser Met Thr Ala Gln Gln Arg
1               5                   10                  15

Ala Ala Leu Ser Glu Glu Phe Ser Arg Ala Ser Arg Thr Thr Thr Ala
                20                  25                  30

Glu Pro Val Ala Val Val Gly Ile Gly Cys Arg Phe Pro Gly Asn Val
            35                  40                  45

Thr Gly Pro Asp Ser Phe Trp Asp Leu Leu Val Glu Gly Gly Asn Ala
        50                  55                  60

Ile Ser Gly Ile Pro Ala Glu Arg Trp Asp Ala Asp Tyr His
65                  70                  75                  80

Pro Asp Pro Leu Thr Pro Gly His Met Thr Thr Lys Trp Gly Ala Phe
                85                  90                  95

Val Ala Asp Ile Ala Gly Phe Asp Ala Glu Phe Phe Gly Ile Thr Pro
            100                 105                 110

Arg Glu Ala Ala Ser Met Asp Pro Gln Gln Arg Met Leu Leu Glu Val
```

```
            115                 120                 125
Thr Trp Glu Ala Leu Glu His Ala Gly Ile Pro Thr Glu Ser Leu Ala
130                 135                 140

Gly Thr Arg Thr Ala Val Met Met Gly Val Tyr Phe Asn Glu Tyr Gln
145                 150                 155                 160

Ser Met Leu Ala Ser Ser Arg Glu Asn Val Asp Ala Tyr Thr Gly Thr
            165                 170                 175

Gly Asn Ser His Ser Ile Thr Ala Gly Arg Ile Ser Tyr Leu Leu Gly
            180                 185                 190

Leu Arg Gly Pro Ala Ala Ala Ile Asp Thr Ala Cys Ser Ser Ser Leu
            195                 200                 205

Ser Ala Ile His Leu Ala Cys Gln Ser Leu Arg Leu Arg Glu Thr Asp
210                 215                 220

Leu Ala Leu Ala Gly Gly Val Ser Ala Thr Leu Arg Pro Glu Thr Gln
225                 230                 235                 240

Ile Ala Ile Ser Ala Trp Gly Leu Leu Ser Pro Glu Gly Arg Cys Ala
            245                 250                 255

Thr Phe Asp Ala Ala Ala Asp Gly Phe Val Arg Gly Glu Gly Ala Gly
            260                 265                 270

Val Val Val Leu Lys Arg Leu Thr Asp Ala Leu Arg Asp Gln Asp Gln
            275                 280                 285

Ile Leu Ala Val Val Arg Gly Ser Ala Val Asn Gln Asp Gly Arg Ser
290                 295                 300

Asn Gly Ile Thr Ala Pro Asn Thr Ala Ala Gln Cys Asp Val Ile Ala
305                 310                 315                 320

Asp Ala Leu Arg Ser Ala Asp Val Ala Pro Glu Ser Val His Tyr Val
            325                 330                 335

Glu Thr His Gly Thr Gly Thr Gln Leu Gly Asp Pro Ile Glu Phe Glu
            340                 345                 350

Ala Leu Ala Ala Thr Tyr Gly Leu Ile Lys Gly Gln Asp Gly Asp Ser
            355                 360                 365

Cys Ala Leu Gly Ala Val Lys Thr Asn Ile Gly His Leu Glu Ala Ala
            370                 375                 380

Ser Gly Val Ala Gly Phe Ile Lys Ala Val Leu Ala Val Gln His Gly
385                 390                 395                 400

Gln Ile Pro Pro Asn Leu His Phe Ser Gln Trp Asn Pro Ala Ile Asp
            405                 410                 415

Ala Ala Ser Thr Arg Leu Phe Val Pro Leu Asp Asn Ile Ala Trp Pro
            420                 425                 430

Ser Asp Ser Gly Pro Arg Arg Ala Ala Val Ser Ser Phe Gly Leu Gly
            435                 440                 445

Gly Thr Asn Ala His Ala Ile Val Glu Gln Gly Pro Glu Leu Ser Pro
            450                 455                 460

Ala Gly Arg Arg Gly Thr Asp Asp Glu Val Thr Thr Leu Val Val Ala
465                 470                 475                 480

Gly Lys Thr Pro Ala Arg Val Ala Ala Thr Ala Gly Met Leu Ala Asp
            485                 490                 495

Trp Met Glu Gly Pro Gly Ala Glu Val Ala Leu Ala Asp Val Ala His
            500                 505                 510

Thr Leu Asn His His Arg Ser Arg Gln Ala Arg Phe Gly Thr Val Val
            515                 520                 525

Ala Arg Glu Arg Ala Gln Ala Val Ala Gly Leu Arg Ala Leu Ala Ala
            530                 535                 540
```

```
Asn Gln His Ala Pro Gly Val Val Asn Pro Ala Asp Ala Pro Pro Glu
545                 550                 555                 560

Pro Gly Thr Val Phe Val Tyr Ser Gly Arg Gly Ser Gln Trp Ala Gly
            565                 570                 575

Met Gly Arg Gln Leu Leu Ala Asp Glu Pro Ala Phe Ala Ala Ala Val
            580                 585                 590

Ala Glu Leu Glu Pro Val Phe Leu Ala Glu Ala Gly Phe Ser Leu His
        595                 600                 605

Asp Val Leu Ala Asn Gly Thr Glu Leu Val Gly Ile Glu Gln Ile Gln
    610                 615                 620

Leu Gly Leu Ile Gly Met Gln Leu Thr Leu Thr Glu Leu Trp Arg Ser
625                 630                 635                 640

Tyr Gly Ile Gln Pro Asp Leu Val Ile Gly His Ser Met Gly Glu Val
                645                 650                 655

Ala Ala Ala Val Val Ala Gly Ala Leu Thr Pro Ala Glu Gly Leu Arg
            660                 665                 670

Val Thr Ala Val Arg Ser Arg Leu Met Ala Pro Leu Ser Gly Gln Gly
        675                 680                 685

Gly Met Ala Leu Leu Gly Leu Asp Ala Ser Gln Thr Glu Ala Leu Ile
690                 695                 700

Ala Asp Tyr Pro Gln Val Thr Leu Gly Ile Tyr Asn Ser Pro Arg Gln
705                 710                 715                 720

Thr Val Ile Ser Gly Pro Thr Asp Gln Ile Asp Glu Leu Ile Thr Val
                725                 730                 735

Val Arg Ala Arg Asp Arg Phe Ala Thr Arg Val Asn Ile Glu Val Ala
            740                 745                 750

Pro His Asn Pro Ala Met Asp Ala Leu Gln Pro Leu Met Arg Ser Glu
        755                 760                 765

Leu Ala Asp Leu Thr Pro Arg Pro Ser Ile Pro Ile Ile Ser Thr
770                 775                 780

Thr Tyr Glu Asp Leu Glu Ser Arg Pro Ala Phe Asp Ala Glu His Trp
785                 790                 795                 800

Ala Thr Asn Met Arg Asn Pro Val Arg Phe Gln Gln Ala Ile Thr His
                805                 810                 815

Ala Phe Asn Gly Ala Asp Thr Ala His His Thr Phe Ile Glu Ile Ser
            820                 825                 830

Ala His Pro Leu Leu Thr His Ala Ile Ser Glu Thr Leu Ala Ala Ser
        835                 840                 845

Gln Asp Ser Ala Gln Gly Glu Thr Asp Ser Gly Ala Ser Tyr Leu Ser
    850                 855                 860

Ile Gly Thr Leu Gln Arg Asp Ala His Asp Thr Leu Thr Phe His Thr
865                 870                 875                 880

Asn Phe Asn Ala Thr His Thr Thr Arg Gly Pro Gln Thr Pro His Pro
                885                 890                 895

Ala Glu Pro His Pro Val Leu Pro Thr Thr Pro Trp Gln His Gly Gln
            900                 905                 910

His Trp Ile Ser Ser Thr Thr Ala Ser Arg Tyr Ala Thr Gly Ser His
        915                 920                 925

Pro Leu Leu Gly Ile Gly Val Thr Asp Pro Thr Asn Gly Thr Arg Val
    930                 935                 940

Trp Glu Ser Gln Leu Gly Pro Asp Leu Leu Trp Leu Ser Asp His Val
945                 950                 955                 960
```

```
Ile Asp Asp Leu Cys Val Leu Pro Gly Ser Ala Tyr Ala Glu Val Ala
                965                 970                 975

Leu Ala Ala Ala Met Asp Thr Phe Lys Asp Ala Glu Gly Asp Gln Gly
            980                 985                 990

Ser Ala Asp Pro Ala Gly Pro Asp  Gly Ser Val Ala Ser  Asn Ala His
        995                 1000                1005

Gln Pro Trp Val Ile Arg Glu Leu Ser Leu His Gln Leu Leu His
    1010                1015                1020

Val Thr Asp Gly Thr Lys Leu Val Thr Thr Leu Thr Gly Asp Glu
    1025                1030                1035

His Thr Cys Arg Ile Glu Ile Ser Thr Gln Ser Gly Ala Ser Gly
    1040                1045                1050

Trp Val Lys His Ala Ser Ala Thr Leu Ala Arg His Asp Ala Ser
    1055                1060                1065

Asp Ser Asp Ala Pro Arg Pro Ala Val Glu Glu Ala Gly Ala Pro
    1070                1075                1080

Thr Asp Glu Leu Asp Pro Glu Gln Leu Tyr Gln Arg Leu Arg Gly
    1085                1090                1095

Ala Gly Gln Gln His Gly Pro Ala Phe Arg Gly Ile Val Gly Leu
    1100                1105                1110

Ala Val Thr Glu Ser Gly Ala Ala Arg Ala Asp Val Arg Leu Pro
    1115                1120                1125

Ser Ser Ala Arg Ile Gly Tyr Arg Gly Phe Ala Leu His Pro Val
    1130                1135                1140

Met Met Asp Ile Ala Val Gln Thr Leu Gly Ala Thr Arg Met Ala
    1145                1150                1155

Leu Glu Leu Ala Glu Gln Gln Asp Ser Gly His Thr Leu Val Leu
    1160                1165                1170

Pro Ile Arg Phe Ala Gly Ile His Val Tyr Gly Asp Ile Ala Glu
    1175                1180                1185

Gly Val Arg Ala Ile Gly Ser Leu Ala Ala Thr Asp Arg Pro Asp
    1190                1195                1200

Arg Leu Val Gly Arg Val Thr Leu Val Asp Pro Asp Gly Gln Pro
    1205                1210                1215

Leu Leu Val Ile Asp Glu Val Glu Met Ala Val Leu Gly Ser Ser
    1220                1225                1230

Ala Ser Pro Thr Glu Leu Thr Ser Arg Leu Phe Thr Leu Glu Trp
    1235                1240                1245

Glu Pro Lys Pro Leu Asp Gln Thr Ala Ala Thr Pro Gly Ala Val
    1250                1255                1260

Leu Leu Ile Gly Asp Leu Gly Ala Asp Asp Arg Leu Leu Pro Ala
    1265                1270                1275

Leu Gln Thr Ser Leu Thr Gly Ser Val Ala Glu Leu Asp Val Val
    1280                1285                1290

Ser Pro Ala Asp Ala Ala Lys Leu Arg Ala Ala Ile Thr Arg Thr
    1295                1300                1305

Asp Ala Arg Trp Gln Asp Ile Val Val Cys Pro Pro Arg Ala
    1310                1315                1320

Val Asp Glu Ala Leu Pro Gln Asp Ala Gln Leu Asp Leu Thr Gln
    1325                1330                1335

Gln Arg Thr Leu Met Ile Ala Asp Val Ala Gln Thr Val Thr Arg
    1340                1345                1350

Met Gly Ala Arg Asn Ser Pro Arg Leu Trp Ile Val Thr Arg Gly
```

```
            1355                1360                1365

Ala Gln Gln Leu Ser Pro Ala Asp Glu Val Thr Leu Ala Gln Thr
            1370                1375                1380

Gln Leu Arg Gly Ile Ala Arg Val Leu Thr Phe Glu His Pro Glu
            1385                1390                1395

Leu Lys Thr Thr Leu Val Asp Ile Glu Gly Asp Gly Glu Gly Ser
            1400                1405                1410

Leu Thr Ala Leu Thr Gln Glu Leu Leu Ala Gly Ala Asp Asp Asp
            1415                1420                1425

Glu Ile Ser Leu Arg Asp Gly Gln Arg Phe Val His Arg Leu Val
            1430                1435                1440

Ala Ala Pro Thr Val Gly Thr Gly Asp Leu Glu Leu Glu Ser Arg
            1445                1450                1455

Arg Thr Val Val Asn Leu Asp Ala Gly Gly Ala Val Gln Leu Arg
            1460                1465                1470

Thr Asp Gln Pro Gly Arg Leu Asp Ser Leu Thr Val His Gln Val
            1475                1480                1485

Lys Arg Cys Arg Pro Gln Gly Asp Gln Val Glu Val Arg Val Ala
            1490                1495                1500

Ala Ala Gly Leu Asn Phe Ser Asp Val Leu Lys Ala Met Gly Val
            1505                1510                1515

Tyr Pro Gly Leu Asp Gly Ala Ala Pro Val Ile Gly Gly Glu Cys
            1520                1525                1530

Val Gly Tyr Val Thr Ala Ile Gly Asp Asp Val Asp Ser Leu Glu
            1535                1540                1545

Ile Gly Gln Arg Val Ile Ala Phe Gly Pro Gly Thr Phe Gly Ser
            1550                1555                1560

His Leu Gly Thr Ile Ala Asp Leu Val Val Pro Ile Pro Asp Thr
            1565                1570                1575

Leu Pro Asp Asn Glu Ala Ala Thr Phe Gly Ile Ala Tyr Leu Thr
            1580                1585                1590

Ala Trp His Ser Leu Cys Glu Val Gly Arg Leu Ser Pro Gly Glu
            1595                1600                1605

Arg Val Leu Ile His Ser Ala Thr Gly Gly Val Gly Met Ala Ala
            1610                1615                1620

Val Ser Ile Ala Lys Met Ile Gly Ala Arg Ile Tyr Thr Thr Ala
            1625                1630                1635

Gly Ser Asp Ala Lys Arg Glu Met Leu Ser Ser Leu Gly Val Asp
            1640                1645                1650

Tyr Val Gly Asp Ser Arg Thr Val Asp Phe Ala Asp Glu Ile Leu
            1655                1660                1665

Glu Leu Thr Asp Gly Tyr Gly Val Asp Ile Val Leu Asn Ser Leu
            1670                1675                1680

Ala Gly Glu Ala Ile Gln Arg Gly Val Gln Ile Leu Ala Pro Gly
            1685                1690                1695

Gly Arg Phe Ile Glu Leu Gly Lys Lys Asp Val His Ala Asn Ala
            1700                1705                1710

Asn Leu Gly Leu Ala Ala Leu Ala Lys Ser Ala Ser Phe Ser Val
            1715                1720                1725

Val Asp Leu Asp Leu Asn Leu Lys Leu Gln Pro Ala Lys Tyr Arg
            1730                1735                1740

Glu Leu Leu Gln Glu Ile Leu Glu His Val Ala Asp Gly Ala Leu
            1745                1750                1755
```

```
Glu Val Leu Pro Val Thr Glu Phe Gly Leu Arg Asp Ala Ala Asp
    1760            1765            1770

Gly Phe Arg Leu Met Ala Ser Gly Lys His Thr Gly Lys Ile Val
    1775            1780            1785

Ile Ser Ile Pro Asp Gly Gly Thr Val Glu Ala Ile Ala Ser Pro
    1790            1795            1800

Pro Pro Glu Pro Leu Val Ser Pro Glu Gly Gly Tyr Leu Ile Val
    1805            1810            1815

Gly Gly Met Gly Gly Leu Gly Phe Val Val Ala Arg Trp Leu Ala
    1820            1825            1830

Glu Gln Gly Ala Gly Leu Ile Val Leu Asn Gly Arg Ser Glu Pro
    1835            1840            1845

Ser Asp Asp Val Arg Ala Ala Ile Ala Asp Leu Ser Ser Gly Gly
    1850            1855            1860

Thr Arg Ile Glu Val Val Thr Gly Asp Ile Ala Glu Pro Gly Thr
    1865            1870            1875

Ala Glu Arg Leu Val Gln Thr Val Gln Asn Ser Gly Phe Arg Leu
    1880            1885            1890

Ala Gly Val Leu His Ser Ala Met Val Leu Asp Asp Glu Ile Val
    1895            1900            1905

Leu Asn Met Ser Glu Ser Ala Ala Arg Arg Val Phe Thr Pro Lys
    1910            1915            1920

Val Ala Gly Ser Trp Arg Leu His Glu Ala Thr Ala Asp Leu Asp
    1925            1930            1935

Leu Asp Trp Trp Leu Thr Phe Ser Ser Val Ala Ser Leu Leu Gly
    1940            1945            1950

Ala Pro Gly Gln Gly Ser Tyr Ala Ala Ala Asn Ser Phe Val Asp
    1955            1960            1965

Gly Leu Val Ala Tyr Arg Arg Ser Leu Gly Leu Pro Ala Val Gly
    1970            1975            1980

Ile Asn Trp Gly Pro Trp Ala Glu Val Gly Arg Ala Gln Phe Phe
    1985            1990            1995

Ala Asp Leu Gly Val Ser Met Ile Thr Val Glu Gln Gly Leu Ala
    2000            2005            2010

Ala Met Gln Leu Val Leu Ser Ala Asp Arg Ala Arg Thr Gly Val
    2015            2020            2025

Phe Ile Leu Asp Ala Arg Gln Trp Phe Gln Ser Phe Pro Ala Ala
    2030            2035            2040

Ala Gly Ser Ser Leu Phe Ser Lys Leu Gln Glu Ser Thr Thr Pro
    2045            2050            2055

Glu Arg Arg Ala Gly Gly Ala Ile Arg Ala Glu Leu Asp Ala Leu
    2060            2065            2070

Glu Gly Ala Ala Ala Ala Glu Arg Pro Ala Arg Leu Ala Ala Ala
    2075            2080            2085

Ile Ala Gly Glu Ile Arg Ala Val Leu Arg Ser Thr Glu Pro Ile
    2090            2095            2100

Asp Val Asp Arg Pro Met Glu Ser Leu Gly Leu Asp Ser Leu Met
    2105            2110            2115

Ala Leu Glu Leu Arg Asn Arg Leu Glu Ala Ser Leu Gly Thr Thr
    2120            2125            2130

Leu Pro Ala Ala Leu Val Trp Ala Tyr Pro Thr Ile Thr Asp Leu
    2135            2140            2145
```

-continued

```
Ala Gly Ala Leu Cys Glu Arg Leu Asp Glu Pro Ala Gly Ala Arg
    2150                2155                2160

Ser Gly Ala Asp Thr Gly Ala Gly Ala Gly Met Phe Arg Ala Leu
    2165                2170                2175

Phe Arg Gln Ala Val Glu Asp Asp Arg Tyr Gly Glu Phe Leu Asp
    2180                2185                2190

Val Leu Ala Glu Ala Ser Ala Phe Arg Pro Gln Phe Ala Ser Pro
    2195                2200                2205

Glu Ala Cys Ser Glu Arg Leu Asp Pro Val Leu Leu Ala Gly Gly
    2210                2215                2220

Pro Thr Asp Arg Ala Glu Gly Arg Ala Val Leu Val Gly Cys Thr
    2225                2230                2235

Gly Thr Ala Ala Asn Gly Gly Pro His Glu Phe Leu Arg Leu Ser
    2240                2245                2250

Thr Ser Phe Gln Glu Glu Arg Asp Phe Leu Ala Val Pro Leu Pro
    2255                2260                2265

Gly Tyr Gly Thr Gly Thr Gly Thr Gly Thr Ala Leu Leu Pro Ala
    2270                2275                2280

Asp Leu Asp Thr Ala Leu Asp Ala Gln Ala Arg Ala Ile Leu Arg
    2285                2290                2295

Ala Ala Gly Asp Ala Pro Val Val Leu Leu Gly His Ser Gly Gly
    2300                2305                2310

Ala Leu Leu Ala His Glu Leu Ala Phe Arg Leu Glu Arg Ala His
    2315                2320                2325

Gly Ala Pro Pro Ala Gly Ile Val Leu Val Asp Pro Tyr Pro Pro
    2330                2335                2340

Gly His Gln Glu Pro Ile Glu Val Trp Ser Arg Gln Leu Gly Glu
    2345                2350                2355

Gly Leu Phe Ala Gly Glu Leu Glu Pro Met Ser Asp Ala Arg Leu
    2360                2365                2370

Leu Ala Met Gly Arg Tyr Ala Arg Phe Leu Ala Gly Pro Arg Pro
    2375                2380                2385

Gly Arg Ser Ser Ala Pro Val Leu Leu Val Arg Ala Ser Glu Pro
    2390                2395                2400

Leu Gly Asp Trp Gln Glu Glu Arg Gly Asp Trp Arg Ala His Trp
    2405                2410                2415

Asp Leu Pro His Thr Val Ala Asp Val Pro Gly Asp His Phe Thr
    2420                2425                2430

Met Met Arg Asp His Ala Pro Ala Val Ala Glu Ala Val Leu Ser
    2435                2440                2445

Trp Leu Asp Ala Ile Glu Gly Ile Glu Gly Ala Gly
    2450                2455                2460

<210> SEQ ID NO 6
<211> LENGTH: 2462
<212> TYPE: PRT
<213> ORGANISM: Artificial Sequence
<220> FEATURE:
<223> OTHER INFORMATION: ppsC-pikTE chimeric enzyme

<400> SEQUENCE: 6

Met Thr Ala Thr Pro Asp Arg Arg Ala Val Ile Thr Asp Ala Leu Arg
1               5                   10                  15

Lys Ile Asp Asp Leu Ser Ala Arg Leu Glu Ile Ala Glu Lys Ala Gly
            20                  25                  30
```

```
Thr Glu Pro Ile Ala Val Val Gly Met Gly Cys Arg Phe Pro Gly Gly
         35                  40                  45

Val Asp Asn Pro Glu Gln Phe Trp Asp Leu Leu His Glu Gly Arg Ser
 50                  55                  60

Gly Ile Val Arg Val Pro Ser Gln Arg Trp Asp Ala Asp Ala Leu Tyr
 65                  70                  75                  80

Thr Asp Asp His Thr Leu Ala Gly Thr Ile Cys Asn Arg Glu Gly Gly
                 85                  90                  95

Phe Leu Ser Thr Trp Glu Pro Ser Glu Phe Asp Ala Glu Phe Phe Ser
            100                 105                 110

Ile Pro Pro Arg Glu Ala Ala Met Asp Pro Gln Gln Arg Leu Phe
        115                 120                 125

Leu Glu Val Ala Trp Glu Ala Leu Glu Asn Ala Gly Ile Pro Pro Gln
130                 135                 140

Thr Ile Arg Gly Thr Gln Thr Gly Val Phe Val Gly Val Thr Ala Tyr
145                 150                 155                 160

Asp Tyr Met Leu Met Met Ser Gly Ala Val Arg Ala Glu Glu Leu Asp
                165                 170                 175

Ala Tyr Leu Leu Thr Gly Asn Ser Ala Asn Phe Ala Ala Gly Arg Thr
            180                 185                 190

Ala Tyr Leu Leu Gly Ala Arg Gly Pro Ala Met Val Leu Asp Thr Ala
        195                 200                 205

Cys Ser Ser Ser Leu Val Ala Ile His Leu Ala Cys Gln Ser Leu Arg
210                 215                 220

Trp Arg Glu Thr Asp Met Ala Leu Val Gly Gly Thr Asn Leu Leu Leu
225                 230                 235                 240

Ser Pro Gly Thr Ser Ile Ala Cys Ser Arg Trp Gly Met Leu Ser Pro
                245                 250                 255

Glu Gly Gln Cys Lys Thr Phe Asp Ala Asp Ala Asp Gly Tyr Val Arg
            260                 265                 270

Ser Glu Gly Ala Gly Val Val Leu Lys Arg Leu Ser Asp Ala Gln
        275                 280                 285

Arg Asp Gly Asn Arg Ile Leu Ala Val Val Arg Gly Ser Ala Val Asn
290                 295                 300

Gln Asp Gly Ala Ser Ser Gly Val Thr Val Pro Asn Gly Pro Ala Gln
305                 310                 315                 320

Gln Ala Leu Leu Ala Gln Ala Leu Asp Ser Ala Lys Leu Thr Pro Ala
                325                 330                 335

Asp Ile Asp Tyr Ile Glu Ala His Gly Thr Gly Thr Pro Leu Gly Asp
            340                 345                 350

Pro Ile Glu Leu Asp Ser Leu Ser Lys Val Phe Ala Asp Arg Glu Gly
        355                 360                 365

Arg Glu Pro Leu Val Leu Gly Ala Val Lys Thr Asn Leu Gly His Leu
370                 375                 380

Glu Ala Ala Ala Gly Ile Ala Gly Phe Met Lys Ser Val Leu Ala Val
385                 390                 395                 400

Gly His Gly Arg Ile Pro Arg Asn Leu Asn Phe Arg Gln Leu Thr Pro
                405                 410                 415

His Ala Ser Glu Gly Val Ser Arg Leu Thr Ile Ala Thr Glu Glu Met
            420                 425                 430

Glu Trp Pro Ala Thr Asp Gln Pro Arg Arg Ala Gly Val Ser Ser Phe
        435                 440                 445

Gly Val Ser Gly Thr Asn Ala His Val Val Ile Glu Gln Ala Pro Asp
```

```
            450             455             460
Pro Ala Pro Val Pro Arg Asp Ala Ala Pro Ala Val Ser Thr Leu Val
465                 470                 475                 480

Val Ser Gly Lys Thr Ala Gln Arg Val Ala Thr Ala Ala Ala Leu
                485                 490                 495

Ala Asp Trp Met Glu Gly Pro Gly Ser Glu Val Pro Leu Ser Asp Val
            500                 505                 510

Ala His Thr Leu Asn His His Arg Ala Arg Gln Pro Lys Phe Ala Thr
            515                 520                 525

Val Ala Ala Val Asp Arg Glu Gln Ala Ile Thr Gly Leu Arg Ala Leu
            530                 535                 540

Ala Ala Gly Glu Pro Ala Thr Gly Val Val Gly Cys Pro Glu Lys Pro
545                 550                 555                 560

Leu Gly Pro Gly Thr Val Phe Val Tyr Ser Gly Arg Gly Ser Gln Trp
                565                 570                 575

Ala Gly Met Gly Arg Gln Leu Leu Ala Asp Glu Pro Ala Phe Ala Ala
            580                 585                 590

Ala Ile Ala Glu Leu Glu Pro Val Phe Leu Ala Glu Ala Gly Phe Ser
            595                 600                 605

Leu His Asp Val Ile Ala Asp Gly Lys Glu Leu Glu Gly Ile Glu Gln
610                 615                 620

Ile Gln Leu Gly Leu Ile Gly Met Gln Leu Ala Leu Thr Ala Leu Trp
625                 630                 635                 640

Arg His Tyr Gly Val Thr Pro Asp Leu Val Ile Gly His Ser Met Gly
                645                 650                 655

Glu Val Ala Ala Thr Val Val Ala Gly Ala Leu Thr Pro Ala Glu Gly
            660                 665                 670

Leu Arg Val Thr Ala Thr Arg Ser Arg Leu Met Ala Pro Leu Ser Gly
            675                 680                 685

Gln Gly Thr Met Ala Met Leu Glu Leu Asp Ala Thr Ala Thr Glu Ala
690                 695                 700

Leu Ile Ala Gly Tyr Pro Glu Val Thr Leu Ala Ile Tyr Ala Ser Pro
705                 710                 715                 720

Arg Gln Thr Val Ile Ala Gly Pro Pro Gln Met Ile Asp Glu Leu Ile
                725                 730                 735

Glu Gln Val Arg Ala Gln Asn Arg Phe Ala Gly Arg Val Asn Ile Glu
            740                 745                 750

Val Ala Pro His Asn Pro Ala Met Asp Ala Leu Gln Pro Leu Met Arg
            755                 760                 765

Ser Glu Leu Ala Asp Leu Thr Pro Arg Pro Ser Ile Pro Ile Ile
770                 775                 780

Ser Thr Thr Tyr Glu Asp Leu Glu Ser Arg Pro Ala Phe Asp Ala Glu
785                 790                 795                 800

His Trp Ala Thr Asn Met Arg Asn Pro Val Arg Phe Gln Gln Ala Ile
                805                 810                 815

Thr His Ala Phe Asn Gly Ala Asp Thr Ala His His Thr Phe Ile Glu
            820                 825                 830

Ile Ser Ala His Pro Leu Leu Thr His Ala Ile Ser Glu Thr Leu Ala
            835                 840                 845

Ala Ser Gln Asp Ser Ala Gln Gly Glu Thr Asp Ser Gly Ala Ser Tyr
850                 855                 860

Leu Ser Ile Gly Thr Leu Gln Arg Asp Ala His Asp Thr Leu Thr Phe
865                 870                 875                 880
```

-continued

```
His Thr Asn Phe Asn Ala Thr His Thr Thr Arg Gly Pro Gln Thr Pro
                885                 890                 895

His Pro Ala Glu Pro His Pro Val Leu Pro Thr Thr Pro Trp Gln His
    900                 905                 910

Gly Gln His Trp Ile Ser Ser Thr Thr Ala Ser Arg Tyr Ala Thr Gly
        915                 920                 925

Ser His Pro Leu Leu Gly Ile Gly Val Thr Asp Pro Thr Asn Gly Thr
    930                 935                 940

Arg Val Trp Glu Ser Gln Leu Gly Pro Asp Leu Leu Trp Leu Ser Asp
945                 950                 955                 960

His Val Ile Asp Asp Leu Cys Val Leu Pro Gly Ser Ala Tyr Ala Glu
                965                 970                 975

Val Ala Leu Ala Ala Ala Met Asp Thr Phe Lys Asp Ala Glu Gly Asp
            980                 985                 990

Gln Gly Ser Ala Asp Pro Ala Gly Pro Asp Gly Ser Val Ala Ser Asn
        995                 1000                1005

Ala His Gln Pro Trp Val Ile Arg Glu Leu Ser Leu His Gln Leu
    1010                1015                1020

Leu His Val Thr Asp Gly Thr Lys Leu Val Thr Thr Leu Thr Gly
    1025                1030                1035

Asp Glu His Thr Cys Arg Ile Glu Ile Ser Thr Gln Ser Gly Ala
    1040                1045                1050

Ser Gly Trp Val Lys His Ala Ser Ala Thr Leu Ala Arg His Asp
    1055                1060                1065

Ala Ser Asp Ser Asp Ala Pro Arg Pro Ala Val Glu Glu Ala Gly
    1070                1075                1080

Ala Pro Thr Asp Glu Leu Asp Pro Glu Gln Leu Tyr Gln Arg Leu
    1085                1090                1095

Arg Gly Ala Gly Gln Gln His Gly Pro Ala Phe Arg Gly Ile Val
    1100                1105                1110

Gly Leu Ala Val Thr Glu Ser Gly Ala Ala Arg Ala Asp Val Arg
    1115                1120                1125

Leu Pro Ser Ser Ala Arg Ile Gly Tyr Arg Gly Phe Ala Leu His
    1130                1135                1140

Pro Val Met Met Asp Ile Ala Val Gln Thr Leu Gly Ala Thr Arg
    1145                1150                1155

Met Ala Leu Glu Leu Ala Glu Gln Gln Asp Ser Gly His Thr Leu
    1160                1165                1170

Val Leu Pro Ile Arg Phe Ala Gly Ile His Val Tyr Gly Asp Ile
    1175                1180                1185

Ala Glu Gly Val Arg Ala Ile Gly Ser Leu Ala Ala Thr Asp Arg
    1190                1195                1200

Pro Asp Arg Leu Val Gly Arg Val Thr Leu Val Asp Pro Asp Gly
    1205                1210                1215

Gln Pro Leu Leu Val Ile Asp Glu Val Glu Met Ala Val Leu Gly
    1220                1225                1230

Ser Ser Ala Ser Pro Thr Glu Leu Thr Ser Arg Leu Phe Thr Leu
    1235                1240                1245

Glu Trp Glu Pro Lys Pro Leu Asp Gln Thr Ala Ala Thr Pro Gly
    1250                1255                1260

Ala Val Leu Leu Ile Gly Asp Leu Gly Ala Asp Asp Arg Leu Leu
    1265                1270                1275
```

```
Pro Ala Leu Gln Thr Ser Leu Thr Gly Ser Val Ala Glu Leu Asp
    1280                1285                1290

Val Val Ser Pro Ala Asp Ala Ala Lys Leu Arg Ala Ala Ile Thr
    1295                1300                1305

Arg Thr Asp Ala Arg Trp Gln Asp Ile Val Val Cys Pro Pro
    1310                1315                1320

Arg Ala Val Asp Glu Ala Leu Pro Gln Asp Ala Gln Leu Asp Leu
    1325                1330                1335

Thr Gln Gln Arg Thr Leu Met Ile Ala Asp Val Ala Gln Thr Val
    1340                1345                1350

Thr Arg Met Gly Ala Arg Asn Ser Pro Arg Leu Trp Ile Val Thr
    1355                1360                1365

Arg Gly Ala Gln Gln Leu Ser Pro Ala Asp Glu Val Thr Leu Ala
    1370                1375                1380

Gln Thr Gln Leu Arg Gly Ile Ala Arg Val Leu Thr Phe Glu His
    1385                1390                1395

Pro Glu Leu Lys Thr Thr Leu Val Asp Ile Glu Gly Asp Gly Glu
    1400                1405                1410

Gly Ser Leu Thr Ala Leu Thr Gln Glu Leu Leu Ala Gly Ala Asp
    1415                1420                1425

Asp Asp Glu Ile Ser Leu Arg Asp Gly Gln Arg Phe Val His Arg
    1430                1435                1440

Leu Val Ala Ala Pro Thr Val Gly Thr Gly Asp Leu Glu Leu Glu
    1445                1450                1455

Ser Arg Arg Thr Val Val Asn Leu Asp Ala Gly Gly Ala Val Gln
    1460                1465                1470

Leu Arg Thr Asp Gln Pro Gly Arg Leu Asp Ser Leu Thr Val His
    1475                1480                1485

Gln Val Lys Arg Cys Arg Pro Gln Gly Asp Gln Val Glu Val Arg
    1490                1495                1500

Val Ala Ala Ala Gly Leu Asn Phe Ser Asp Val Leu Lys Ala Met
    1505                1510                1515

Gly Val Tyr Pro Gly Leu Asp Gly Ala Ala Pro Val Ile Gly Gly
    1520                1525                1530

Glu Cys Val Gly Tyr Val Thr Ala Ile Gly Asp Asp Val Asp Ser
    1535                1540                1545

Leu Glu Ile Gly Gln Arg Val Ile Ala Phe Gly Pro Gly Thr Phe
    1550                1555                1560

Gly Ser His Leu Gly Thr Ile Ala Asp Leu Val Val Pro Ile Pro
    1565                1570                1575

Asp Thr Leu Pro Asp Asn Glu Ala Ala Thr Phe Gly Ile Ala Tyr
    1580                1585                1590

Leu Thr Ala Trp His Ser Leu Cys Glu Val Gly Arg Leu Ser Pro
    1595                1600                1605

Gly Glu Arg Val Leu Ile His Ser Ala Thr Gly Gly Val Gly Met
    1610                1615                1620

Ala Ala Val Ser Ile Ala Lys Met Ile Gly Ala Arg Ile Tyr Thr
    1625                1630                1635

Thr Ala Gly Ser Asp Ala Lys Arg Glu Met Leu Ser Ser Leu Gly
    1640                1645                1650

Val Asp Tyr Val Gly Asp Ser Arg Thr Val Asp Phe Ala Asp Glu
    1655                1660                1665

Ile Leu Glu Leu Thr Asp Gly Tyr Gly Val Asp Ile Val Leu Asn
```

```
                    1670                1675                1680
Ser Leu Ala Gly Glu Ala Ile Gln Arg Gly Val Gln Ile Leu Ala
                    1685                1690                1695

Pro Gly Gly Arg Phe Ile Glu Leu Gly Lys Lys Asp Val His Ala
        1700                1705                1710

Asn Ala Asn Leu Gly Leu Ala Ala Leu Ala Lys Ser Ala Ser Phe
        1715                1720                1725

Ser Val Val Asp Leu Asp Leu Asn Leu Lys Leu Gln Pro Ala Lys
        1730                1735                1740

Tyr Arg Glu Leu Leu Gln Glu Ile Leu Glu His Val Ala Asp Gly
        1745                1750                1755

Ala Leu Glu Val Leu Pro Val Thr Glu Phe Gly Leu Arg Asp Ala
        1760                1765                1770

Ala Asp Gly Phe Arg Leu Met Ala Ser Gly Lys His Thr Gly Lys
        1775                1780                1785

Ile Val Ile Ser Ile Pro Asp Gly Gly Thr Val Glu Ala Ile Ala
        1790                1795                1800

Ser Pro Pro Pro Glu Pro Leu Val Ser Pro Glu Gly Gly Tyr Leu
        1805                1810                1815

Ile Val Gly Gly Met Gly Gly Leu Gly Phe Val Val Ala Arg Trp
        1820                1825                1830

Leu Ala Glu Gln Gly Ala Gly Leu Ile Val Leu Asn Gly Arg Ser
        1835                1840                1845

Glu Pro Ser Asp Asp Val Arg Ala Ala Ile Ala Asp Leu Ser Ser
        1850                1855                1860

Gly Gly Thr Arg Ile Glu Val Val Thr Gly Asp Ile Ala Glu Pro
        1865                1870                1875

Gly Thr Ala Glu Arg Leu Val Gln Thr Val Gln Asn Ser Gly Phe
        1880                1885                1890

Arg Leu Ala Gly Val Leu His Ser Ala Met Val Leu Asp Asp Glu
        1895                1900                1905

Ile Val Leu Asn Met Ser Glu Ser Ala Ala Arg Arg Val Phe Thr
        1910                1915                1920

Pro Lys Val Ala Gly Ser Trp Arg Leu His Glu Ala Thr Ala Asp
        1925                1930                1935

Leu Asp Leu Asp Trp Trp Leu Thr Phe Ser Ser Val Ala Ser Leu
        1940                1945                1950

Leu Gly Ala Pro Gly Gln Gly Ser Tyr Ala Ala Ala Asn Ser Phe
        1955                1960                1965

Val Asp Gly Leu Val Ala Tyr Arg Arg Ser Leu Gly Leu Pro Ala
        1970                1975                1980

Val Gly Ile Asn Trp Gly Pro Trp Ala Glu Val Gly Arg Ala Gln
        1985                1990                1995

Phe Phe Ala Asp Leu Gly Val Ser Met Ile Thr Val Glu Gln Gly
        2000                2005                2010

Leu Ala Ala Met Gln Leu Val Leu Ser Ala Asp Arg Ala Arg Thr
        2015                2020                2025

Gly Val Phe Ile Leu Asp Ala Arg Gln Trp Phe Gln Ser Phe Pro
        2030                2035                2040

Ala Ala Ala Gly Ser Ser Leu Phe Ser Lys Leu Gln Glu Ser Thr
        2045                2050                2055

Thr Pro Glu Arg Arg Ala Gly Gly Ala Ile Arg Ala Glu Leu Asp
        2060                2065                2070
```

```
Ala Leu Glu Gly Ala Ala Ala Glu Arg Pro Ala Arg Leu Ala
    2075                2080            2085

Ala Ala Ile Ala Gly Glu Ile Arg Ala Val Leu Arg Ser Thr Glu
    2090                2095            2100

Pro Ile Asp Val Asp Arg Pro Met Glu Ser Leu Gly Leu Asp Ser
    2105                2110            2115

Leu Met Ala Leu Glu Leu Arg Asn Arg Leu Glu Ala Ser Leu Gly
    2120                2125            2130

Thr Thr Leu Pro Ala Ala Leu Val Trp Ala Tyr Pro Thr Ile Thr
    2135                2140            2145

Asp Leu Ala Gly Ala Leu Cys Glu Arg Leu Asp Glu Pro Ala Gly
    2150                2155            2160

Ala Arg Ser Gly Ala Asp Thr Gly Ala Gly Ala Gly Met Phe Arg
    2165                2170            2175

Ala Leu Phe Arg Gln Ala Val Glu Asp Asp Arg Tyr Gly Glu Phe
    2180                2185            2190

Leu Asp Val Leu Ala Glu Ala Ser Ala Phe Arg Pro Gln Phe Ala
    2195                2200            2205

Ser Pro Glu Ala Cys Ser Glu Arg Leu Asp Pro Val Leu Leu Ala
    2210                2215            2220

Gly Gly Pro Thr Asp Arg Ala Glu Gly Arg Ala Val Leu Val Gly
    2225                2230            2235

Cys Thr Gly Thr Ala Ala Asn Gly Gly Pro His Glu Phe Leu Arg
    2240                2245            2250

Leu Ser Thr Ser Phe Gln Glu Glu Arg Asp Phe Leu Ala Val Pro
    2255                2260            2265

Leu Pro Gly Tyr Gly Thr Gly Thr Gly Thr Gly Thr Ala Leu Leu
    2270                2275            2280

Pro Ala Asp Leu Asp Thr Ala Leu Asp Ala Gln Ala Arg Ala Ile
    2285                2290            2295

Leu Arg Ala Ala Gly Asp Ala Pro Val Val Leu Leu Gly His Ser
    2300                2305            2310

Gly Gly Ala Leu Leu Ala His Glu Leu Ala Phe Arg Leu Glu Arg
    2315                2320            2325

Ala His Gly Ala Pro Pro Ala Gly Ile Val Leu Val Asp Pro Tyr
    2330                2335            2340

Pro Pro Gly His Gln Glu Pro Ile Glu Val Trp Ser Arg Gln Leu
    2345                2350            2355

Gly Glu Gly Leu Phe Ala Gly Glu Leu Glu Pro Met Ser Asp Ala
    2360                2365            2370

Arg Leu Leu Ala Met Gly Arg Tyr Ala Arg Phe Leu Ala Gly Pro
    2375                2380            2385

Arg Pro Gly Arg Ser Ser Ala Pro Val Leu Leu Val Arg Ala Ser
    2390                2395            2400

Glu Pro Leu Gly Asp Trp Gln Glu Glu Arg Gly Asp Trp Arg Ala
    2405                2410            2415

His Trp Asp Leu Pro His Thr Val Ala Asp Val Pro Gly Asp His
    2420                2425            2430

Phe Thr Met Met Arg Asp His Ala Pro Ala Val Ala Glu Ala Val
    2435                2440            2445

Leu Ser Trp Leu Asp Ala Ile Glu Gly Ile Glu Gly Ala Gly
    2450                2455            2460
```

HOST CELLS AND METHODS FOR PRODUCING ALKYL LACTONE BY CYCLIZATION OF HYDROXYL FATTY ACID

RELATED PATENT APPLICATIONS

The application claims priority as a continuation-in-part application to International Patent Application No. PCT/US2018/49609, filed Sep. 5, 2018, which in turn claims priority to U.S. Provisional Patent Application Ser. No. 62/554,428, filed Sep. 5, 2017, both of which are herein incorporated by reference in their entireties.

STATEMENT OF GOVERNMENTAL SUPPORT

The invention was made with government support under Contract Nos. DE-AC02-05CH11231 awarded by the U.S. Department of Energy. The government has certain rights in the invention.

FIELD OF THE INVENTION

The present invention is in the field of production of natural alkyl lactones and esters from sugars using non-natural combinations of enzymes in cell-free reactions or microbial hosts.

BACKGROUND OF THE INVENTION

Currently there is a need for a renewable, consolidated bio-based route to alkyl lactones. Alkyl lactones are both economically and environmentally very valuable. Examples of valuable alkyl lactones include hexadecanolide, pentadecanolide, ambrettolide, gamma- and delta-hexalactone, gamma- and delta-octalactone, gamma- and delta-decalactone, gamma- and delta-dodecalactone, and gamma- and delta-tetradecalactone. Many of these compounds are fine fragrances or flavor compounds. Currently there are synthetic and semi-synthetic paths for synthesizing these chemicals which rely on the use of expensive or toxic reagents. Some of these compounds, or their synthetic precursors, can be isolated from natural sources like plants and shellac. The price of these natural resources can vary significantly depending on climate and other uncontrollable factors. What is needed is an engineered microbe that produces valuable alkyl lactones directly from renewable feedstocks like glucose or glycerol.

Hydroxy acids are the biocatalytic precursors of alkyl lactones. Currently, hydroxy acids are isolated from natural sources, or more commonly, produced biologically via hydroxylation of fatty acids by a cytochrome P450 enzyme. This process has been described previously. Once hydroxy fatty acids are in hand, the cyclization of these compounds to produce alkyl lactones is typically achieved through chemical synthesis. Acid-catalyzed cyclization can be achieved when substrate concentrations are low, but the necessity for a dilute reaction mixture makes scale up challenging. Catalysts based on metals such as Hafnium have been reported to cyclize hydroxy fatty acids. Another method involves esterification of an alcohol and an acid, each bearing a terminal alkene, followed by ring-closing metathesis (RCM), which is dependent on a Ruthenium-based catalyst. Delta-hydroxy fatty acids, or 5-hydroxy acids, are a particularly valuable group of hydroxyl acids because delta-lactones can be produced from delta-hydoxy acids.

Esters are another group of valuable compounds. Many of these compounds are fine fragrances or flavor compounds. It is desirable to market these compounds as "natural". There is a need for a microbe that produces natural esters directly from renewable feedstocks like natural sugar cane.

SUMMARY OF THE INVENTION

This present invention provides for a genetically modified host cell, or a cell-free reaction system, and related methods and materials for the biocatalytic production of an alkyl lactones from a hydroxy fatty acid, or natural alkyl lactones and esters from sugars using non-natural combinations of enzymes. In some embodiments, the hydroxy fatty acid is a saturated hydroxy fatty acid or an unsaturated hydroxyl fatty acid. In some embodiments, the unsaturated hydroxy is a polyunsaturated hydroxy fatty acid. In some embodiments, the lactone is a delta lactone, such as any delta lactone described herein.

The genetically modified host cell comprises (a) (i) a fatty acid activating enzyme which converts a carboxyl of the hydroxyl fatty acid into a thioester, and (ii) an ester-forming enzyme which converts the thioester into an alkyl lactone, or (b) (i) an enzyme which converts the hydroxyl fatty acid into a coenzyme A-bound thioester, and (ii) an esterase which acts on a fatty acid-coA which converts the coenzyme A-bound thioester into an alkyl lactone, or (c) (i) an enzyme which converts the hydroxyl fatty acid into an acyl carrier protein-bound thioester, and (ii) an esterase or thioesterase which converts the acyl carrier protein-bound thioester into an alkyl lactone. These enzymes are collectively termed "alkyl lactone forming enzymes".

In some embodiments, the cell-free reaction system comprises: (a) (i) a fatty acid activating enzyme which converts a carboxyl of a hydroxyl fatty acid into a thioester, and (ii) an ester-forming enzyme which converts the thioester into an alkyl lactone, or (b) (i) an enzyme which converts the hydroxyl fatty acid into a coenzyme A-bound thioester, and (ii) an esterase which acts on a fatty acid-coA which converts the coenzyme A-bound thioester into an alkyl lactone, or (c) (i) an enzyme which converts the hydroxyl fatty acid into an acyl carrier protein-bound thioester, and (ii) an esterase or thioesterase which converts the acyl carrier protein-bound thioester into an alkyl lactone.

The present invention provides for a method for producing an alkyl lactone in a microbe by altering the expression of one or more genes encoding the alkyl lactone forming enzymes.

BRIEF DESCRIPTION OF THE DRAWINGS

The foregoing aspects and others will be readily appreciated by the skilled artisan from the following description of illustrative embodiments when read in conjunction with the accompanying drawings.

DETAILED DESCRIPTION OF THE INVENTION

Figure 1:
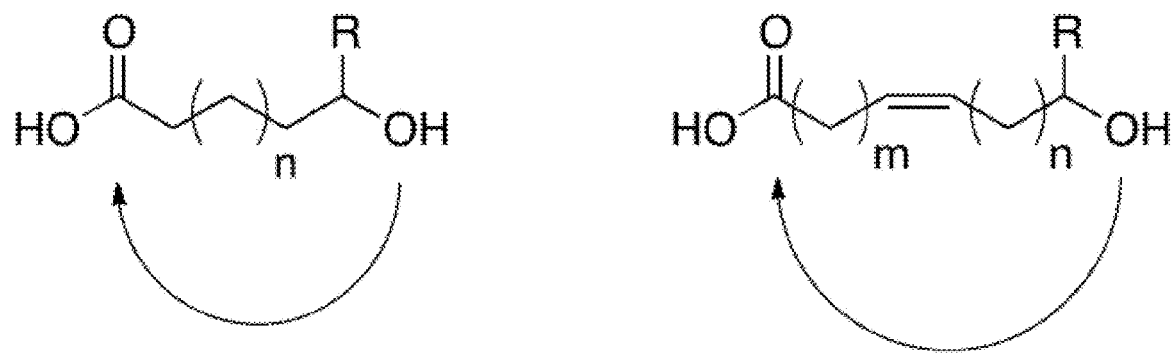
FIG. 1 shows the producing of an alkyl lactone via formation of a C—O bond between the terminal hydroxyl and the carboxyl groups of the hydroxyl fatty acid via intramolecular nucleophilic attack.

Before the invention is described in detail, it is to be understood that, unless otherwise indicated, this invention is not limited to particular sequences, expression vectors, enzymes, host microorganisms, or processes, as such may vary. It is also to be understood that the terminology used herein is for purposes of describing particular embodiments only, and is not intended to be limiting.

In this specification and in the claims that follow, reference will be made to a number of terms that shall be defined to have the following meanings:

The terms "optional" or "optionally" as used herein mean that the subsequently described feature or structure may or may not be present, or that the subsequently described event or circumstance may or may not occur, and that the description includes instances where a particular feature or structure is present and instances where the feature or structure is absent, or instances where the event or circumstance occurs and instances where it does not.

The term "5-hydroxy acid" is a delta hydroxy acid.

The terms "hydroxyl fatty acid" and "hydroxy fatty acid" have the same meaning.

The term "delta lactone" includes all chemical species of the following structures:

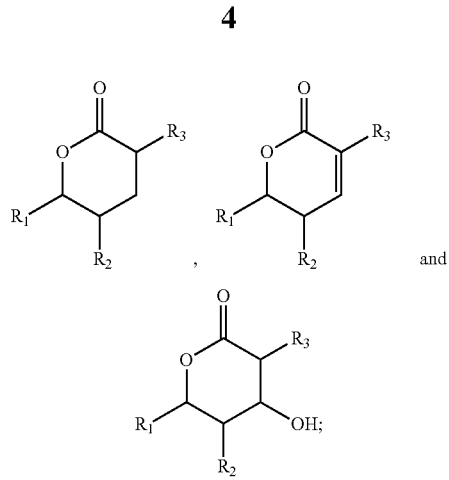

including, but not limited to, wherein $R_1$ is -isopropyl, -2-methylbutyryl or sec-butyryl, 3-methylbutyryl or -isobutyryl, n-butyl, or any hydrocarbon chain comprising 4-10 carbons; $R_2$ is —H, —CH$_3$, or —CH$_2$CH$_3$; and, $R_3$ is —H, —CH$_3$, or —CH$_2$CH$_3$. In some embodiments, the "delta lactone" is any one of the following:

R1=isopropyl; R2=—H, R3=—H

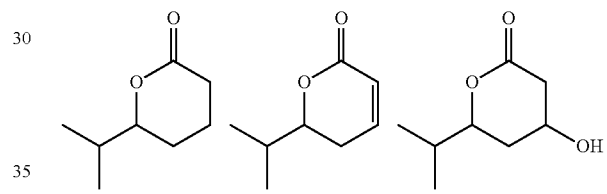

R1=2-methylbutyryl, R2=—H, R3=—H

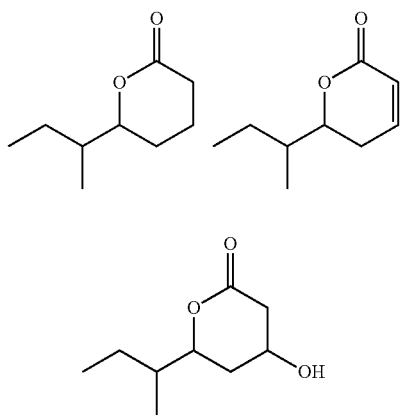

R3-methylbutyryl, R2=—H, R3=—H

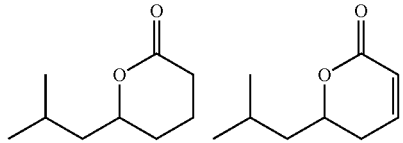

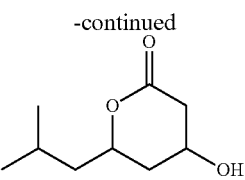

R1=hydrocarbon chain 4-10 carbons, R2=—H, R3=—H

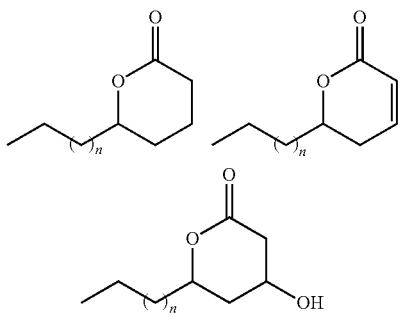

wherein n is an integer from 2 to 8.

The term "acyl group" refers to any molecule comprising a carbonyl carbon bound to an oxygen, sulfur, or nitrogen, including, but not limited to, fatty acids, hydroxy fatty acids, acyl-coAs, and acyl-ACPs.

The term "extension module" refers to a polyketide synthase enzyme, or a fragment of a polyketide synthase enzyme, that catalyzes condensation of malonyl-coA or methylmalonyl-coA with an acyl group.

The term "fully reducing extension module" refers to a polyketide synthase enzyme, or a fragment of a polyketide synthase enzyme, that comprises ketoreductase, dehydratase, and enoyl reductase domains and results in a methylene (—$CH_2$—) group at the 3 position in the acyl group produced.

This present invention provides for a genetically modified host cell and related methods and materials for the biocatalytic production of an alkyl lactones from a hydroxy fatty acid. In some embodiments, the hydroxy fatty acid is a saturated hydroxy fatty acid or an unsaturated hydroxyl fatty acid. In some embodiments, the hydroxy fatty acid is a polyunsaturated hydroxy fatty acid.

The genetically modified host cell comprises (a) (i) a fatty acid activating enzyme which converts a carboxyl of the hydroxyl fatty acid into a thioester, and (ii) an ester-forming enzyme which converts the thioester into an alkyl lactone, or (b) (i) an enzyme which converts the hydroxyl fatty acid into a coenzyme A-bound thioester, and (ii) an esterase which acts on a fatty acid-coA which converts the coenzyme A-bound thioester into an alkyl lactone, or (c) (i) an enzyme which converts the hydroxyl fatty acid into an acyl carrier protein-bound thioester, and (ii) an esterase or thioesterase which converts the acyl carrier protein-bound thioester into an alkyl lactone. These enzymes are collectively termed "alkyl lactone forming enzymes".

In some embodiments, the esterase or thioesterase which converts the acyl carrier protein-bound thioester into an alkyl lactone is a non-natural PKS enzyme comprising a chimeric fusion of PpsC from *Mycobacterium marinum* operably linked to a thioesterase domain from any PKS. In some embodiments, the esterase or thioesterase which converts the acyl carrier protein-bound thioester into an alkyl lactone is a non-natural PKS enzyme comprising a chimeric fusion of PpsC from *Mycobacterium marinum* operably linked to a thioesterase domain from (1) erythromycin PKS, (2) pikromycin PKS, or (3) Pks13 from *Gibberella zeae*.

The present invention provides for a genetically modified host cell comprising one or more non-native polyketide synthase (PKS) enzymes, wherein said host cell is capable of converting a suitable carbon source into a caprolactone derivative.

In some embodiments, the genetically modified host cell comprises: (a) a first non-natural PKS enzyme that produces a 6-hydroxy fatty acid or caprolactone derivative, and optionally (b) a second non-natural PKS enzyme that produces a 4-hydroxy acyl group that is operably linked to the first non-natural PKS enzyme, and optionally (c) a PKS loading module capable of loading a 2-hydroxy acyl group.

In some embodiments, the saturated hydroxy fatty acid has the following chemical structure:

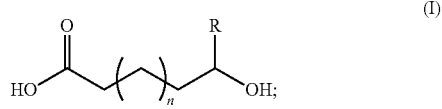

(I)

wherein n is an integer from one to 20, and R is H or an akyl chain having a chain length of C1 to C10. In some embodiments, where n is an integer from one to 2, 3, 4, 5, 6, 7, 8, 9, 10, 11, 12, 13, 14, 15, 16, 17, 18, or 19.

In some embodiments, the unsaturated hydroxy fatty acid has the following chemical structure:

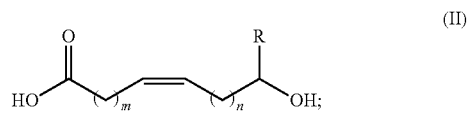

(II)

wherein m is an integer from one to 20, n is an integer from one to 20, and R is H or an akyl chain having a chain length of C1 to C10. In some embodiments, m is an integer from one to 2, 3, 4, 5, 6, 7, 8, 9, 10, 11, 12, 13, 14, 15, 16, 17, 18, or 19. In some embodiments, n is an integer from zero to 1, 2, 3, 4, 5, 6, 7, 8, 9, 10, 11, 12, 13, 14, 15, 16, 17, 18, or 19. In some embodiments, m+n=14. In some embodiments, m is an integer from one to 14, n is an integer from zero to 13, and m+n=14.

In some embodiments, the fatty acid activating enzyme is an acyl-acyl-carrier protein synthetases (AASs), fatty acyl-AMP ligases (FAALs), or fatty acyl-coenzyme A ligases (FACLs).

In some embodiments, the ester-forming enzyme an esterase or thioesterase, such as a cyclizing thioesterase (cycTE) enzyme.

In some embodiments, the esterase which acts on a fatty acid-coA is PapA5 from mycobacteria, or a wax ester synthase enzyme.

The alkyl lactone can be produced via formation of a C—O bond between the terminal hydroxyl group and the carboxyl group of the hydroxyl fatty acid via intramolecular nucleophilic attack. See FIG. 1.

Figure 2:
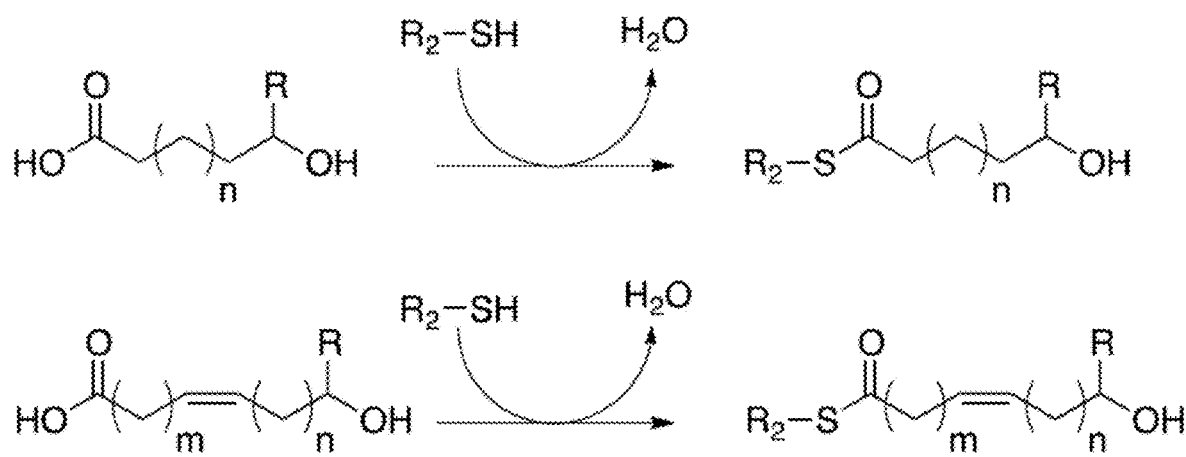
FIG. 2 shows the conversion of a carboxy end of the hydroxyl fatty acid into a thioester group.

This process can be facilitated enzymatically. First, the carboxy end of the hydroxyl fatty acid is converted to a thioester group. See FIG. 2.

Figure 3:
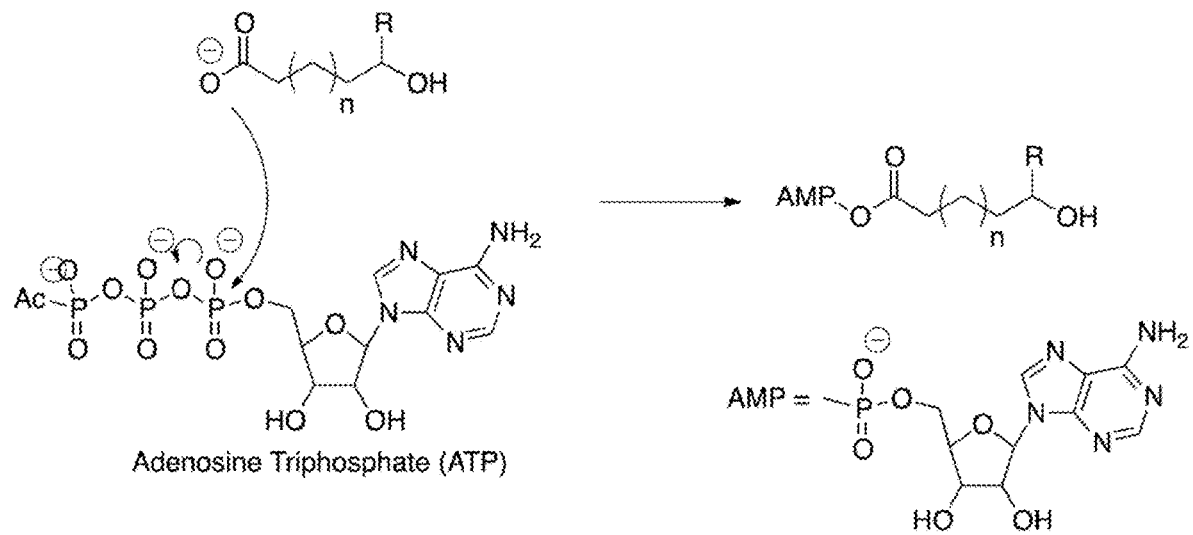
FIG. 3 shows the conversion of a fatty acid carboxylate group into an adenosine monophosphate (AMP) mixed anhydride using the cofactor adenosine triphosphate (ATP).

Converting the carboxyl group in hydroxyl fatty acids to thioesters could be achieved by fatty acid activating enzymes. Several classes of enzymes, referred to as acyl-acyl-carrier protein synthetases (AASs), fatty acyl-AMP ligases (FAALs), or fatty acyl-coenzyme A ligases (FACLs) could potentially be leveraged for this purpose. These enzymes catalyze thioester formation in two steps. In step 1, the fatty acid carboxylate group is converted to an adenosine monophosphate (AMP) mixed anhydride using the cofactor adenosine triphosphate (ATP). See FIG. 3.

Figure 4:
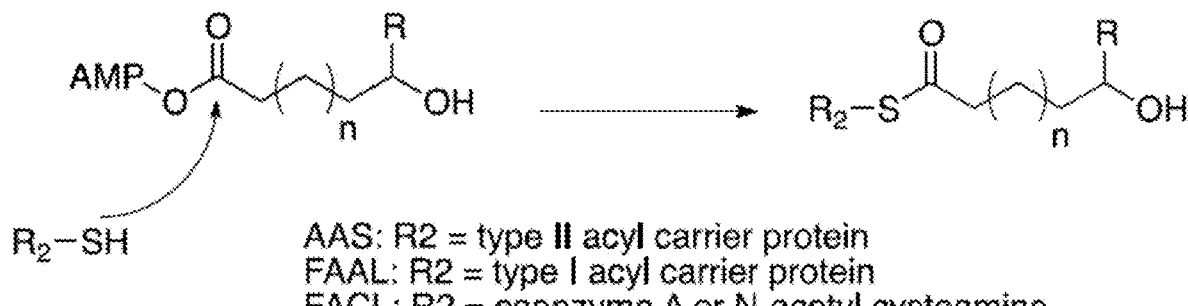
FIG. 4 shows the conversion of an AMP-anhydride intermediate into the corresponding thioester by nucleophilic attack of a coenzyme A, N-acetyl cysteamine, or the 4'phosphopantetheine prosthetic group of an acyl carrier protein.

This AMP-anhydride intermediate is then converted to the corresponding thioester by nucleophilic attack of a coenzyme A, N-acetyl cysteamine, or the 4'phosphopantetheine prosthetic group of an acyl carrier protein. See FIG. 4.

Figure 5:
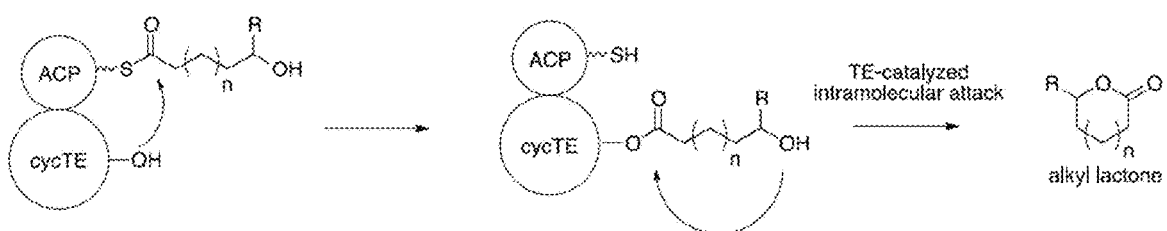
FIG. 5 shows cyclizing thioesterase (cycTE) enzymes catalyze lactone formation on substrates bound to an acyl carrier protein domain that is part of the same polypeptide as the cycTE.

Once thioester formation is achieved, lactone formation can be catalyzed by a variety of ester-forming enzymes, referred to as esterases or thioesterases. Some cyclizing thioesterase (cycTE) enzymes could catalyze lactone formation on substrates bound to an acyl carrier protein domain that is part of the same polypeptide as the cycTE. See FIG. 5.

Figure 6:
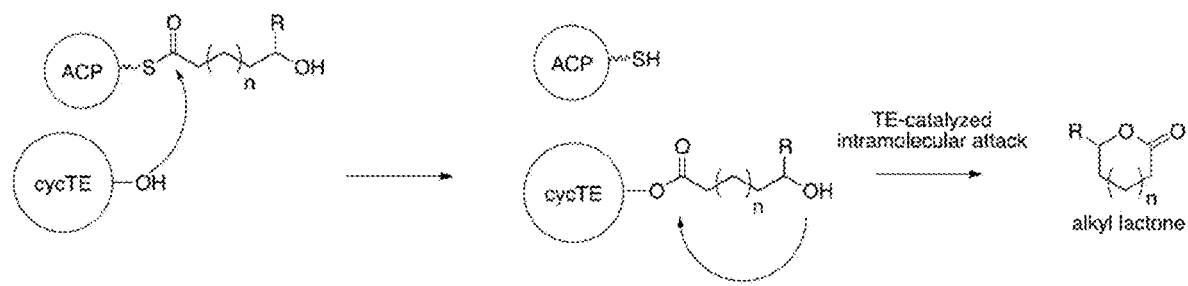
FIG. 6 shows cycTE catalyzes cyclization of substrates bound to acyl carrier proteins that are discrete, or part of a separate polypeptide.

In some embodiments, a cycTE catalyzes cyclization of substrates bound to acyl carrier proteins that are discrete, or part of a separate polypeptide. See FIG. 6.

Figure 7:
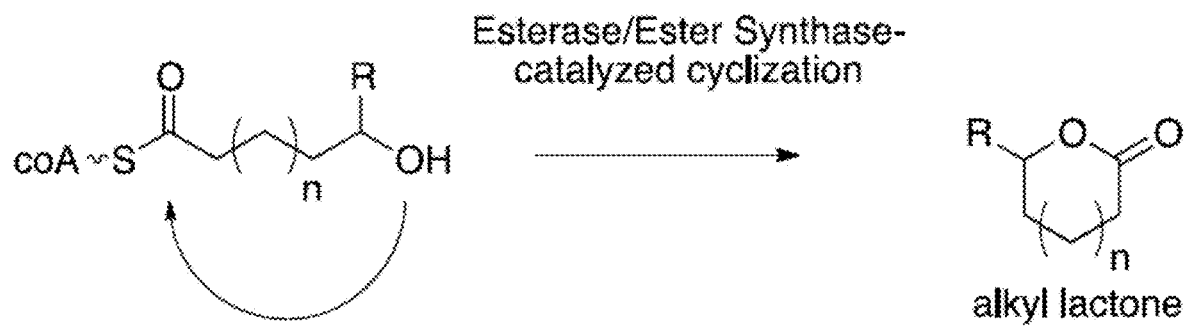
FIG. 7 shows hydroxy fatty acids are converted to coenzyme A-bound thioesters, and lactone formation is catalyzed by an esterase that operates on fatty acyl-coAs.

In some embodiments, hydroxy fatty acids are converted to coenzyme A-bound thioesters, and lactone formation is catalyzed by an esterase that operates on fatty acyl-coAs. One example of this would be PapA5 from mycobacteria, or wax ester synthase enzymes. See FIG. 7.

Figure 8:
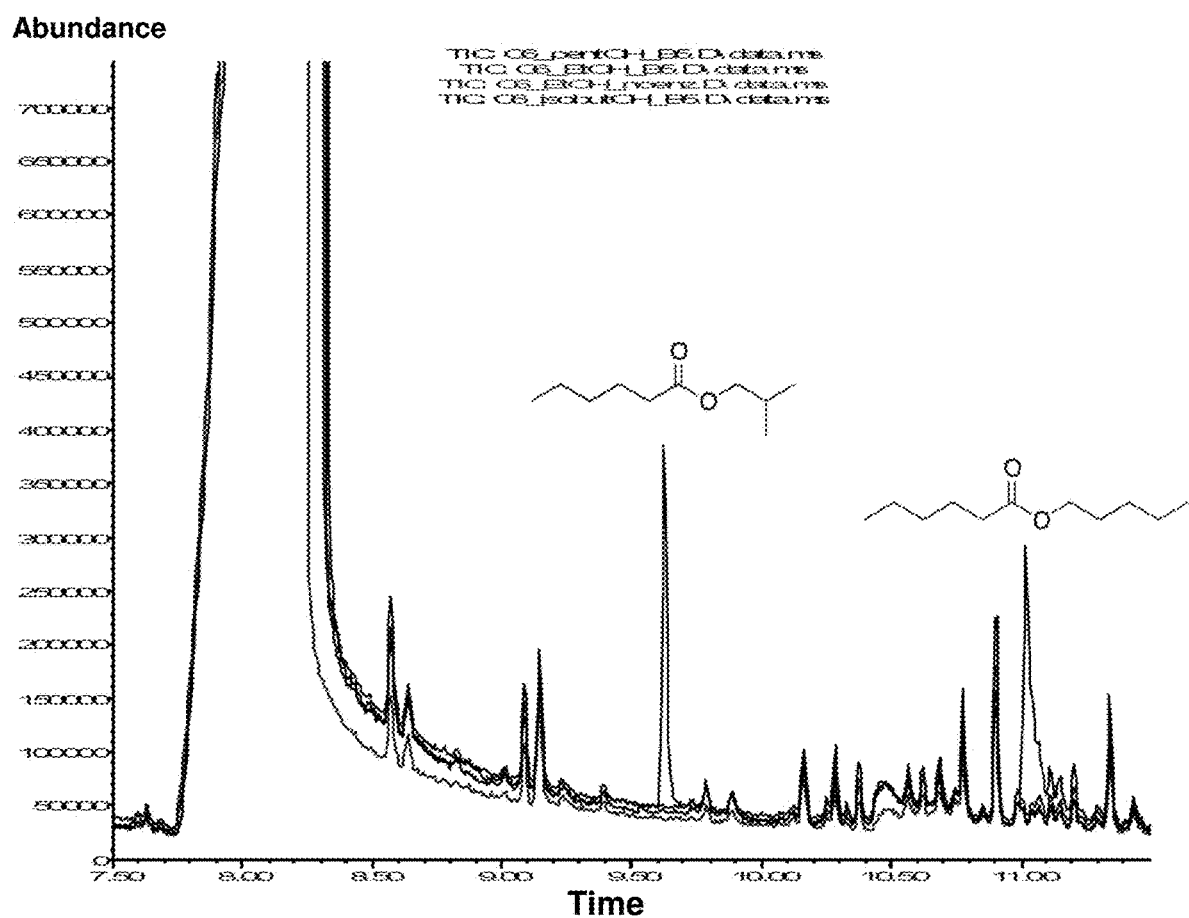
FIG. 8 shows the successful production of esterified C6 fatty acid with isobutyryl alcohol and n-pentanol from the "vhAAS+acpP-zeaTE" chimeric enzyme.
Figure 9:
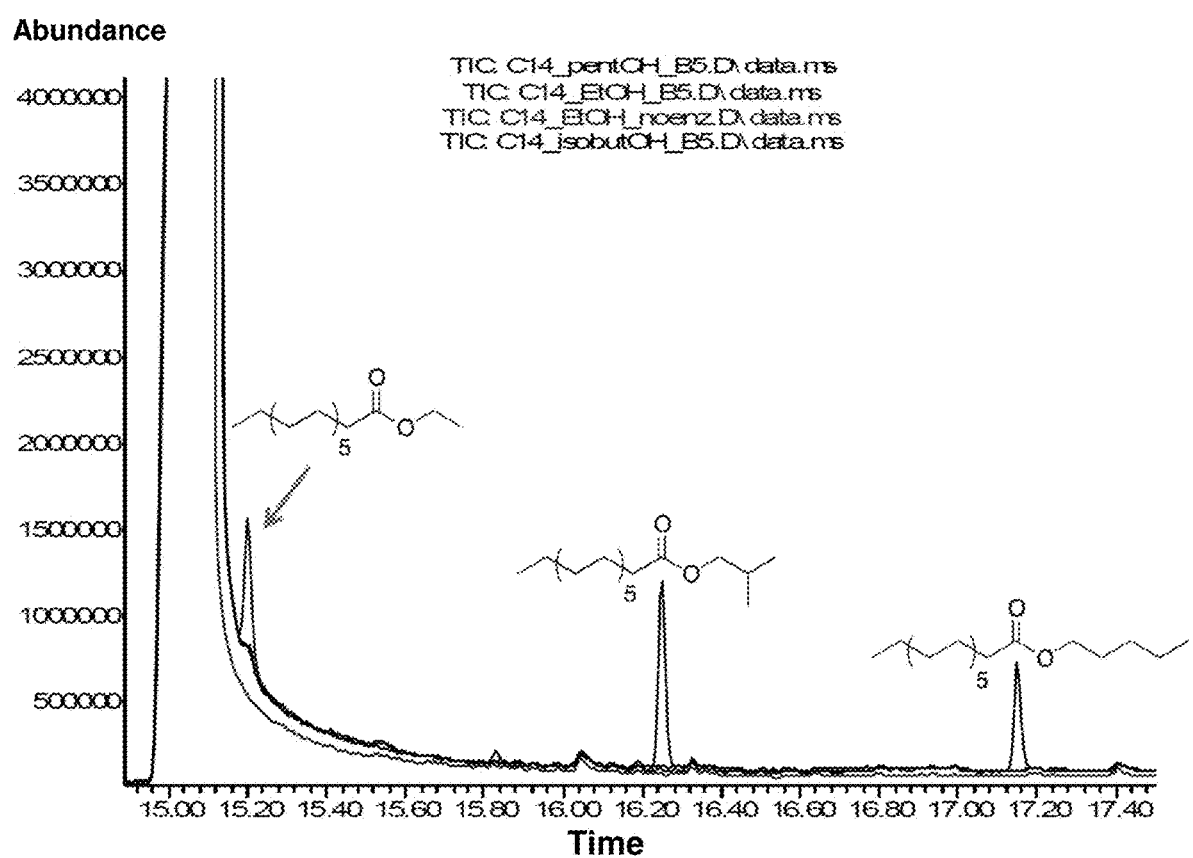
FIG. 9 shows the successful production of esterified C14 fatty acid with ethanol, isobutyryl alcohol and n-pentanol from the "vhAAS+acpP-zeaTE" chimeric enzyme.
Figure 10:
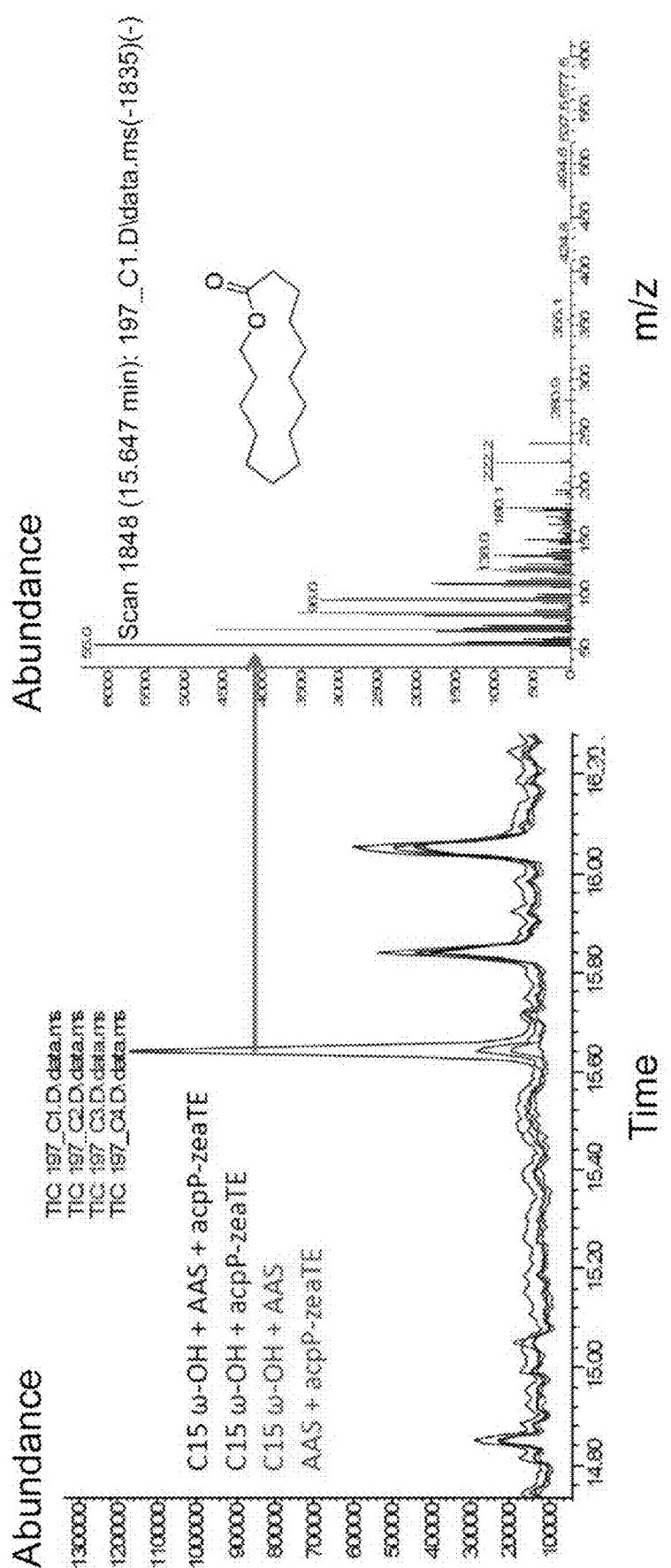
FIG. 10 shows the successful production of esterified C15 ω-OH fatty acid from the "vhAAS+acpP-zeaTE" chimeric enzyme.

FIGS. 8-10 show the substrate diversity of the "vhAAS+ acpP-zeaTE" chimeric enzyme, and the successful production of esterified fatty acid.

Figure 11:
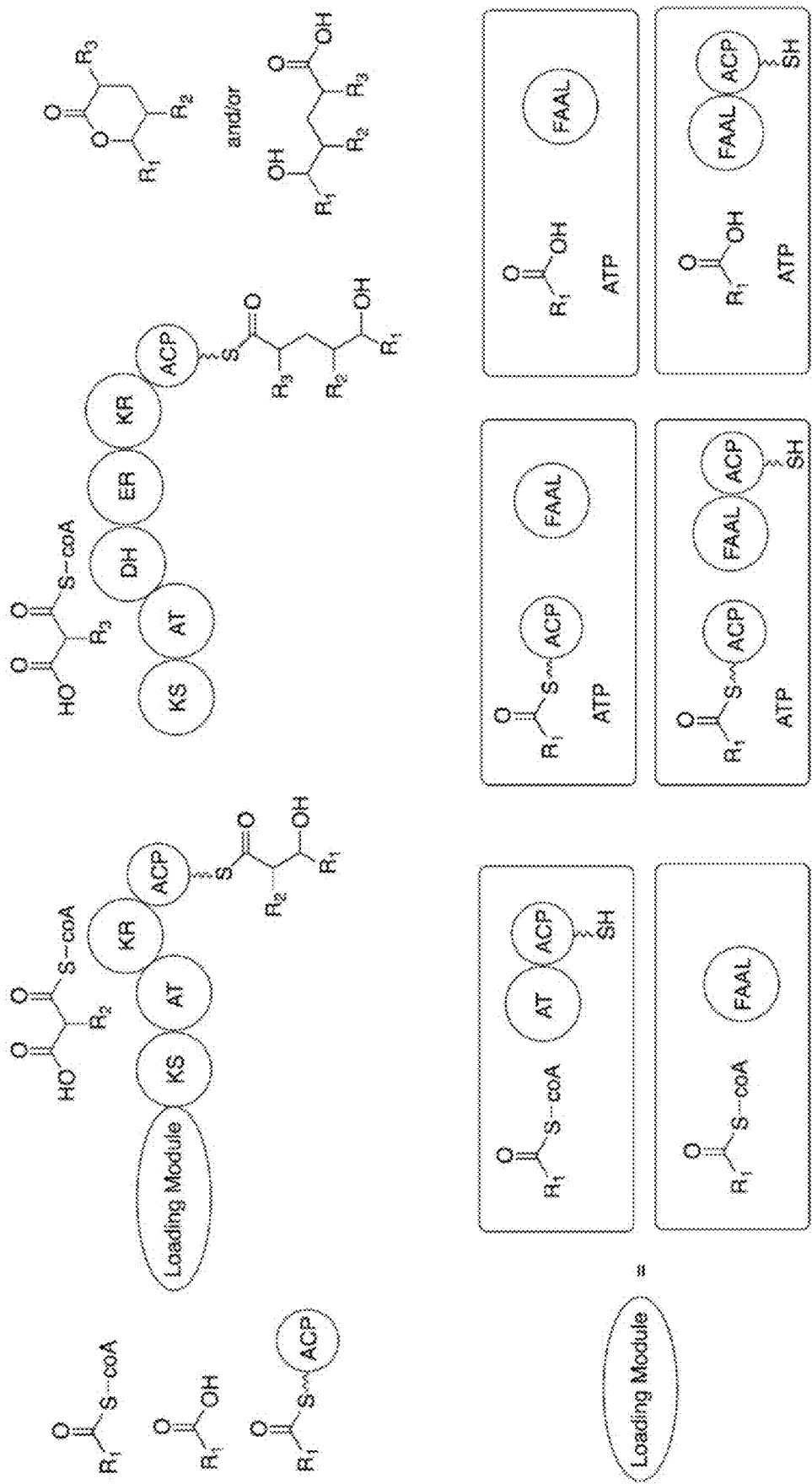
FIG. 11 shows the scheme for delta lactone (δ-lactone) production using PKS, and examples of loading modules. $R_1$ can be a fatty acid of any length. The reaction can start with an acyl-CoA, fatty acid, or acyl ACP. The loading modules are all known ways of loading. Compounds with shorter $R_2$ and $R_3$ chains, such as methyl, are useful as fuels. Compounds with $R_2$ and $R_3$ are H, and $R_1$ is a longer chain, are useful as lubricants.

FIG. 11 shows the scheme for delta lactone (δ-lactone) production using PKS, and examples of loading modules. $R_1$ can be a fatty acid of any length. The reaction can start with an acyl-CoA, fatty acid, or acyl ACP. The loading modules are all known ways of loading. Compounds with shorter $R_2$ and $R_3$ chains, such as methyl, are useful as fuels. Compounds with $R_2$ and $R_3$ are H, and $R_1$ is a longer chain, are useful as lubricants.

Figure 12:
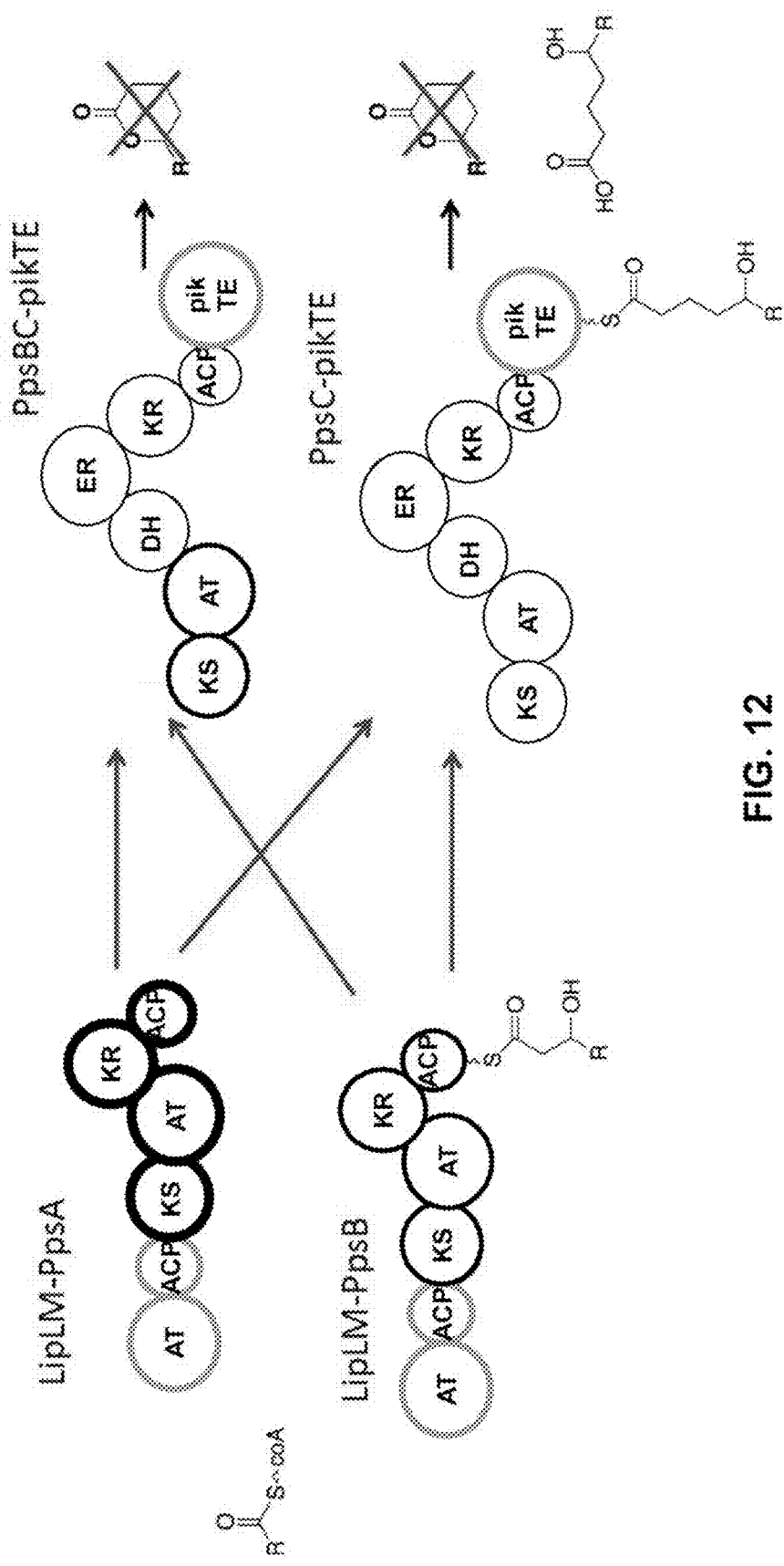
FIG. 12 shows the reactions catalyzed by the enzymes shown herein. LipLM-ppsA and LipLM-ppsB are upstream modules, which have been expressed and purified.

FIG. 12 shows the reactions catalyzed by the enzymes shown herein. LipLM-ppsA and LipLM-ppsB are upstream modules, which have been expressed and purified.

An examples of a chimeric protein reduced to practice is: PpSA+lipomycin piece.

The PKS modules pass the reactant sequentially. The PpsA plus PpSB has KR loading module. PpsC has full reducing loop to get fully reduced C. PpSA+PpsBC C8CoA extended once, and some situations release a C12 delta hydroxy acid. LipLM works on shorter fatty acid chains (C3-C4). PpsA, B, and C naturally take C20-C22 substrates. The C14 lactone has a buttery flavor. The C10-C12 lactones are commercially valuable.

Many of the enzymatic activities described above have not been previously reported, or reported to have been performed on different substrates. The in vivo activation of hydroxy fatty acids to coA- or acyl carrier protein-thioesters in a recombinant organism have never been previously reported. None of the fatty acid activating enzymes described herein have been shown to operate on hydroxy fatty acids in their native biological environments; rather, they operate on fatty acids or fatty acids containing para-hydroxy benzoyl groups. Therefore, use of these enzymes for activation of hydroxy acids in recombinant cells represents a completely novel biosynthetic pathway.

Further, enzymatic cyclization of endogenously-produced hydroxy fatty acids using cycTE, esterase, or ester synthase enzymes has also not been previously reported. cycTEs typically operate on polyketide synthase substrates that are produced by completely different means than hydroxy acids. Esterase and ester synthase enzymes have only been reported to catalyze intermolecular esterification, that is, ester formation between a hydroxyl group and a thioester group from separate molecules. These enzymes have not been previously reported to operate on substrates where intramolecular cyclization is possible, as is the case with hydroxy acyl-coAs. Therefore, this invention is novel because it depends on one or more non-natural and unproved enzymatic steps. This invention is a novel method for producing alkyl lactones.

The present invention provides for a recombinant or genetically modified host cell, such as a recombinant or genetically modified of *E. coli*, that is capable of producing one or more alkyl lactone from a carbon source, such as glucose, acetate, propionate or glycerol, or a combination thereof.

In some embodiments, the unsaturated hydroxy acid is polyunsaturated.

In some embodiments, the fatty acid activating enzyme is an acyl-acyl-carrier protein synthetase (AAS) from *Vibrio harveyii*. In some embodiments, the ester-forming enzyme is a thioesterase from Pks13 of *Gibberella zeae*.

The present invention also provides for a non-natural fusion protein comprising an acyl carrier domain from a type II fatty acid synthase or type II polyketide synthase operably linked to a thioesterase domain of a type I polyketide synthase. The non-natural fusion protein comprises an N-terminal acyl carrier protein domain.

In some embodiments, the N-terminal acyl carrier protein domain is the acyl carrier protein from *Escherichia coli* fatty acid synthase. In some embodiments, the thioesterase domain is a thioesterase from Pks13 from *Gibberella zeae*.

The present invention also provides for a genetically modified host cell comprising one or more non-native polyketide synthase (PKS) enzymes, wherein said host cell is capable of converting a suitable carbon source into a 5-hydroxy acid or delta lactone, or a non-natural PKS enzyme that produces a caprolactone derivative.

The present invention also provides for a non-natural PKS enzyme that produces a caprolactone derivative.

In some embodiments, the genetically modified host cell comprises a non-natural PKS enzyme that produces a 5-hydroxy fatty acid or delta lactone. In some embodiments, the 5-hydroxy fatty acid or delta lactone comprises six or more, seven or more, or eight or more carbon atoms. In some embodiments, the delta lactone is not a delta lactone having any of the following chemical structure:

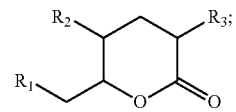

wherein $R^1$ is H or —$CH_3$; $R^2$ and $R^3$ are each independently H, —$CH_3$, or —$CH_2CH_3$.

In some embodiments, the genetically modified host cell comprises: (a) a first non-natural PKS enzyme that produces a 5-hydroxy fatty acid or delta lactone comprising six or more, seven or more, or eight or more carbon atoms, and optionally (b) a second non-natural PKS enzyme that produces a 3-hydroxy acyl group that is operably linked to the first non-natural PKS enzyme.

In some embodiments, the first non-natural PKS enzyme comprises a chimeric fusion of PpsB and PpsC from *Mycobacterium marinum* operably linked to a thioesterase domain from erythromycin PKS.

In some embodiments, the first non-natural PKS enzyme comprises a chimeric fusion of PpsB and PpsC from *Mycobacterium marinum* operably linked to a thioesterase domain from pikromycin PKS.

In some embodiments, the first non-natural PKS enzyme comprises a chimeric fusion of PpsB and PpsC from *Mycobacterium marinum* operably linked to a thioesterase domain from Pks13 from *Gibberella zeae.*

In some embodiments, the first non-natural PKS enzyme comprises a chimeric fusion of PpsC from *Mycobacterium marinum* operably linked to a thioesterase domain from erythromycin PKS.

In some embodiments, the first non-natural PKS enzyme comprises a chimeric fusion of PpsC from *Mycobacterium marinum* operably linked to a thioesterase domain from pikromycin PKS.

In some embodiments, the first non-natural PKS enzyme comprises a chimeric fusion of PpsC from *Mycobacterium marinum* operably linked to a thioesterase domain from Pks13 from *Gibberella zeae.*

In some embodiments, the second non-natural PKS enzyme comprises a loading module of lipomycin PKS1 operably linked to PpsA from *Mycobacterium marinum.*

In some embodiments, the second non-natural PKS enzyme comprises a loading module of lipomycin PKS1 operably linked to PpsB from *Mycobacterium marinum.*

In some embodiments, the host cell comprises one or more non-native polyketide synthase enzymes comprising non-natural combinations of peptides from the mycolactone PKS from *Mycobacterium ulcerans.*

In some embodiments, the 5-hydroxy acid or delta lactone comprises a cis-double bond.

In some embodiments, the 5-hydroxy acid is 5-hydroxy decanoic acid, 5-hydroxy dodecanoic acid, 5-hydroxy tetradecanoic acid, 5-hydroxy-cis-2-decenoic acid, and 5-hydroxy-cis-2-dodecenoic acid.

In some embodiments, the delta lactone is delta decalactone, delta dodecalactone, delta tetradecalactone, and massoia lactone.

The present invention also provides for a non-natural polyketide synthase (PKS) enzyme comprising a fully reducing extension module operably linked to a thioesterase domain that produces a 5-hydroxy acid or delta lactone when expressed in a host cell.

The present invention also provides for a non-natural PKS enzyme that produces a cis-2-unsaturated 5-hydroxy acid or a 2, 3 unsaturated delta lactone.

The present invention also provides for a non-natural PKS enzyme that produces a 3-hydroxy acyl group comprising six or more carbons.

The present invention also provides for a genetically modified host cell comprising: (a) a fatty acid activating enzyme which converts a carboxyl of a fatty acid into a thioester, and (b) an ester-forming enzyme which converts the thioester into an alkyl ester in the presence of an alcohol.

In some embodiments, the fatty acid activating enzyme is vhAAS and the ester-forming enzyme is a non-natural fusion protein comprising an acyl carrier domain from a type II fatty acid synthase or type II polyketide synthase operably linked to a thioesterase domain of a type I polyketide synthase.

In some embodiments, the fatty acid activating enzyme is vhAAS, or the AAS enzyme from *E. coli, Bacillus subtilis*, or any other bacteria with a type II FAS ACP synthetase ester-forming enzyme is a non-natural fusion protein comprising an acyl carrier domain from a type II fatty acid synthase or type II polyketide synthase operably linked to a thioesterase domain of a type I polyketide synthase.

In some embodiments, the fatty acid activating enzyme is vhAAS and the ester-forming enzyme is acpP-zeaTE.

In some embodiments, the alcohol is ethanol, n-propanol, isopropanol, n-butanol, isobutanol, 2-methylbutanol, n-pentanol, isopentanol, hexanol and octanol.

The genetically modified host cells are capable, when cultured, to produce an alkyl lactone.

The present invention provides for a method for producing an alkyl lactone in a microbe by altering the expression of one or more genes encoding the alkyl lactone forming enzymes.

The amino acid sequence of "vhAAS" is as follows:

(SEQ ID NO: 1)

```
MNQYVNDPSNYQLLIKNLLFSPVAFNPEQEIVYANHRRHSYKTFHDRVRQ
FANALTKMGVKKGDTVAVMDYDSHRYLECYFAIPMIGAKLHMINVRLSPE
QILYTIDHAEDDIILIHEEFLPILDQIKGRIDTVTRYVVLRDDEECEYER
LLEQESTEYNFPDFDENTVATTFYTTGTTGFPKGVFFTHRQLVLHTMGIL
STIGTNASQGRLHQGDIYMPITPMFHVHAWGLPYMATMLGVKQVYPGKYV
PDVLLNLIEQEKVTFSHCVPTILHLLLSSPKSKAMDFSGWKVVIGGAALP
KALCKSALERDIDVFAGYGMSETGPILSIVQLTPEQLELDVDQQAEYRSK
TGKKVALVEAYIVDEDMNKLPHDGETAGEIVVRAPWLTPNYYKDNKNSKA
LWRGGYLHTGDVAHIDDEGFIKITDRVKDMIKISGEWVSSLELEDILHQH
QSVSEVAVIGMPHNKWGEVPLALVTLKEDAQVTEKELLGFAKDFINKGIL
AREALLLKVKIVDEIAKTSVGKVDKKELRKLHL*
```

The amino acid sequence of "acpP zeaTE" is as follows:

(SEQ ID NO: 2)

```
MSTIEERVKKIIGEQLGVKQEEVTNNASFVEDLGADSLDTVELVMALEEE
FDTEIPDEEAEKITTVQAAIDYPAIGDLRRVFAPKSTHISLDNDLSRPSL
VDDTSQALQSSGSESFDQPPTSVTSTSDSGSIVKIDLGPDVDSPAPKIKI
TLLQGRPGNGRTPFYLIADGTGTIATYIHLPQFKSQIPIYGIDSPFLRCP
TRFTTDVGITGAARFITEALMKAQPEGTFVLGGFSGGAMLAYEVCRQLAA
ANRKVDSLMLIDMCSPRSKTVEDKNDIGWAIFESISRQNGLWRSTDMTRQ
HLQAIFAAVATYHPQPLKASERPKRTAIIWAEKGMIDRCAGDSELMQKLA
KRGIPTEPYPKFMEDSELGPVAWGLPHKTKNDLGPNGWERYVGDALCLSM
PADHLEMPMPGHVHLLHEKMTRAFEFFNEAG*
```

The amino acid sequence of "lipLM-ppsA" is as follows:

(SEQ ID NO: 3)

```
MSEHRGSAGGSVLFPRTGTVLPWVLTGPGAAAVRARSEALRTHLRASTEW
SPAGVGQALLAGTGAGADTHRAVVLAGDRAQTLNALAALSAGADHPAVFT
STRADASPAGPVFVFPGQGSQWTGMARELLDSAPVFARKLHDCADAFAPY
LGHSLLDSVTGAAGGPEPVGADVVQPALFAVMVALTDLWNAAGVAPGALL
GHSLGELAAAHVAGVLSLDDSARVVARWSQAQATLAGRGDMVSVLLPADE
LADLLDRRWPGRLVVAVENGPGSAVASGDLDAAAELVAHLTAEGIHARRV
DVGLAAHSPHIDAILPRIRADIAPIRAHTPSIPVYSALHGGALDGTPMDA
AYWCRNLRSTVRFADATRAALEAGHTTFVEVSPHPVLTTAMEVSATRAAH
```

```
AATVLGTLRRGEGGPSRFLASLAELHVSGGDADLRTVLPASQAAGLPETV
LTAGPRGESADGDSRHEVLCARLAPLDPAERRAQLLTVVRESAAAALDGD
DQGSIDGRRTFRDLGITSLAAVGIRDRLHSATGLRLSPTVVFDHPTPDAL
AAHLDTELFGTGADAEPAPAAGGRAVPHDEPIAVVGMGCRFPGGISGPEA
LWQFLCDRKSSIGRVPDERWAQFDDGSPAVKALLARTTRWGSYLTDIDAF
DADFFEISASEADKMDPQQRLLLEVAWEALEHAGIPPSSLRRSQTGVFAG
SCLSEYGAIASTDLTQVDGWSNTGGAMSIIANRLSYFLDLRGPSVAVDTA
CSSSLVAIHLACQSLRMQDSNLAIAAGVNLLLSPAVFRGFDQVGALSPTG
NCRAFDAAADGFVRGEGAGVVVLKRLTDAQQDGDRVLAVICGSAINQDGR
SNGLMAPNPAAQQAVLRAAYTNAGMQPSEVDYVEAHGTGTLLGDPIEARA
LGSVLGRGRPEESPLLIGAVKTNLGHTEAAAGIAGFIKAVLAVQHGRIPP
NQRFESPNPHIAFADLRMKVVDELTDWPDTGHPRRAGVSSFGFGGTNAHV
VIEQGQEAASSPEAGLTPALSTLVVAGKTPARVAATAGMLADWMEGPGAE
VALADVAHTLNHHRSRQARFGTVVARERAQAVAGLRALAANQHAPGVVNP
ADAPPEPGTVFVYSGRGSQWAGMGRQLLADEPVFAAAVAELEPVFLAEAG
FSLHDVLANGTELVGIEQIQLGLIGMQLTLTELWRSYGIQPDLVIGHSMG
EVAAAVVAGALTPAEGLRVTAVRSRLMAPLSGQGGMALLELDASQTEALI
ADYPQVTLGIYNSPRQTVISGPTDQIDELITVVRARDRFATRVNIEVAPH
NPAMDALQPQMRSELADLAPRTPTIPIISTTYADLGSARESGPTFDAEHW
AINMRNPVHFQQAITAAATDKHNFIEISAHPLLTQAILETLHTVQPGSKY
TSLGTLQRDSDDTIVERTNLNTVRTAPPQTPHPPEPHPQIPTTPWHHTHH
WIDTPAVASRSASTPDKDAAGSSEPSVSGDSDDAVDSCHYRVGWPTKPLA
DAKASTETASGTRWLVFADAELGAELGLAAGAQTRVDVIDPSALTEESEL
LAALAGVEHVVYAPPAGKSLDVNAAYQLFHQVRRLVTVMTKASLTAKLLL
VTRNAQPIAEGDRANPAHGVLWGLGRTIALEHPEIWRGIIDLDESMPAEL
AAPKILGEVTGTDGEDQVVYRCGGRHVPRLQRRTAPAVAPVTLDPNSSQL
VIGATGNIGPYLIRQLAQMGAKTVVAVSRNPGQRLQELAESLAAEGTNLV
IEAADATDEAAMTALFDRFGADLPPLEGIYLAAFAGGPVLLNEMTDADVR
AMFAPKLDAAALLHRLSLKVPARHFVLFSSISGLIGSRWLAHYTATSGYL
DALAYARHALGLPATTVNWGLWKSLADAEHDASQVSVGSGLLPMQDEVAI
GTLPLLMNPAAGVHSVVVEADWPLLAAAYRTRGSLHIVDDLLRDFAEAST
IPARDWSHLSAQEVRTEFEAGLRRIVARELRVSESDLETDRPLAELGLNS
LMAMAIRREAEMFVGIELSATMLFNHPTVASLASYLANRVAPQDNSSNDQ
MAELSASAGSTLDSLFDRIESSSLLPEGPG*
```

The amino acid sequence of "lipLM-ppsB" is as follows:

```
                                           (SEQ ID NO: 4)
MSEHRGSAGGSVLFPRTGTVLPWVLTGPGAAAVRARSEALRTHLRASTEW
SPAGVGQALLAGTGAGADTHRAVVLAGDRAQTLNALAALSAGADHPAVFT
STRADASPAGPVFVFPGQGSQWTGMARELLDSAPVFARKLHDCADAFAPY
LGHSLLDSVTGAAGGPEPVGADVVQPALFAVMVALTDLWNAAGVAPGALL
GHSLGELAAAHVAGVLSLDDSARVVARWSQAQATLAGRGDMVSVLLPADE
LADLLDRRWPGRLVVAVENGPGSAVASGDLDAAAELVAHLTAEGIHARRV
DVGLAAHSPHIDAILPRIRADIAPIRAHTPSIPVYSALHGGALDGTPMDA
AYWCRNLRSTVRFADATRAALEAGHTTFVEVSPHPVLTTAMEVSATRAAH
AATVLGTLRRGEGGPSRFLASLAELHVSGGDADLRTVLPASQAAGLPETV
LTAGPRGESADGDSRHEVLCARLAPLDPAERRAQLLTVVRESAAAALDGD
DQGSIDGRRTFRDLGITSLAAVGIRDRLHSATGLRLSPTVVFDHPTPDAL
AAHLDTELFGTGADAEPAPAAGGRAVPHDEPVAVVGIGCRFPGNVTGPDS
FWDLLVEGGNAISGIPAERWDADDYYHPDPLTPGHMTTKWGAFVADIAGF
DAEFFGITPREAASMDPQQRMLLEVTWEALEHAGIPTESLAGTRTAVMMG
VYFNEYQSMLASSRENVDAYTGTGNSHSITAGRISYLLGLRGPAAAIDTA
CSSSLSAIHLACQSLRLRETDLALAGGVSATLRPETQIAISAWGLLSPEG
RCATFDAAADGFVRGEGAGVVVLKRLTDALRDQDQILAVVRGSAVNQDGR
SNGITAPNTAAQCDVIADALRSADVAPESVHYVETHGTGTQLGDPIEFEA
LAATYGLIKGQDGDSCALGAVKTNIGHLEAASGVAGFIKAVLAVQHGQIP
PNLHFSQWNPAIDAASTRLFVPLDNIAWPSDSGPRRAAVSSFGLGGTNAH
AIVEQGPELSPAGRRGTDDEVTTLVVAGKTPARVAATAGMLADWMEGPGA
EVALADVAHTLNHHRSRQARFGTVVARERAQAVAGLRALAANQHAPGVVN
PADAPPEPGTVFVYSGRGSQWAGMGRQLLADEPAFAAAVAELEPVFLAEA
GFSLHDVLANGTELVGIEQIQLGLIGMQLTLTELWRSYGIQPDLVIGHSM
GEVAAAVVAGALTPAEGLRVTAVRSRLMAPLSGQGGMALLGLDASQTEAL
IADYPQVTLGIYNSPRQTVISGPTDQIDELITVVRARDRFATRVNIEVAP
HNPAMDALQPQMRSELADLAPRTPTIPIISTTYADLGSARESGPTFDAEH
WAINMRNPVHFQQAITAAATDKHNFIEISAHPLLTQAILETLHTVQPGSK
HTCLGTLQRDSDDTIVFRTNLNTVRTAPPQTPHPPEPHPQIPTTPWHHTH
HWIDNAASSSPALSRSESRDGTGAALDTRWSPESGSLLDEWSHKVVWAAQ
SLPDTPSAQTAVHGRWLVLGNADLAAELGRGADVLDSDSEPAALARALSD
VDYVLYAPPVPADPLDVAEAYQLFHQARRLATAMIANGSPAKLLIATRNA
QPIAEGDPANPSHGVLWGLGRTITLEHPEIWGAIIDFDNSVPAQVVARQV
LDEADATDSEDQVVYRSGVRHVPRLRRHSLAAQPVALDAGASQLVIGATG
NIGPHLINQLAEMGAKTIVAVSRNPGQRLQKLAESLAAEGVNLVIAAADA
TDEAAMTALFDRFGADLPPLEGIYLAAFAGQPVLLTEMTNDDVTAMFAPK
LDAAALLHRLSLKVPVRHFVLFSSISGLIGSRWLAHYTATSGYLDALAYA
RRVMGLPATTVNWGLWKSLADAEHDASQVSLGSGLVPMQDDVAIGALPLV
MSQAAGVHSVVVAADWPLLAAAYRTRGSLRIVDDVLPVSDETTVLESEFR
VALRNCAPERRHDMLHDQVAMLAANVMGLHAGESLDPSTGFFQLGMDSLM
SVTLQRALSDSLGEFLPPSVVFDYPTVYSLTDYLATILPELETDDESTAD
VYDELTEAELLEQLSQRLRGT*
```

The amino acid sequence of "ppsBC-pikTE" is as follows:

(SEQ ID NO: 5)
MRSVYSRISSMTAQQRAALSEEFSRASRTTTAEPVAVVGIGCRFPGNVTG
PDSFWDLLVEGGNAISGIPAERWDADDYYHPDPLTPGHMTTKWGAFVADI
AGFDAEFFGITPREAASMDPQQRMLLEVTWEALEHAGIPTESLAGTRTAV
MMGVYFNEYQSMLASSRENVDAYTGTGNSHSITAGRISYLLGLRGPAAAI
DTACSSSLSAIHLACQSLRLRETDLALAGGVSATLRPETQIAISAWGLLS
PEGRCATFDAAADGFVRGEGAGVVVLKRLTDALRDQDQILAVVRGSAVNQ
DGRSNGITAPNTAAQCDVIADALRSADVAPESVHYVETHGTGTQLGDPIE
FEALAATYGLIKGQDGDSCALGAVKTNIGHLEAASGVAGFIKAVLAVQHG
QIPPNLHFSQWNPAIDAASTRLFVPLDNIAWPSDSGPRRAAVSSFGLGGT
NAHAIVEQGPELSPAGRRGTDDEVTTLVVAGKTPARVAATAGMLADWMEG
PGAEVALADVAHTLNHHRSRQARFGTVVARERAQAVAGLRALAANQHAPG
VVNPADAPPEPGTVFVYSGRGSQWAGMGRQLLADEPAFAAAVAELEPVFL
AEAGFSLHDVLANGTELVGIEQIQLGLIGMQLTLTELWRSYGIQPDLVIG
HSMGEVAAAVVAGALTPAEGLRVTAVRSRLMAPLSGQGGMALLGLDASQT
EALIADYPQVTLGIYNSPRQTVISGPTDQIDELITVVRARDRFATRVNIE
VAPHNPAMDALQPLMRSELADLTPRPPSIPIISTTYEDLESRPAFDAEHW
ATNMRNPVRFQQAITHAFNGADTAHHTFIEISAHPLLTHAISETLAASQD
SAQGETDSGASYLSIGTLQRDAHDTLTFHTNFNATHTTRGPQTPHPAEPH
PVLPTTPWQHGQHWISSTTASRYATGSHPLLGIGVTDPTNGTRVWESQLG
PDLLWLSDHVIDDLCVLPGSAYAEVALAAAMDTFKDAEGDQGSADPAGPD
GSVASNAHQPWVIRELSLHQLLHVTDGTKLVTTLTGDEHTCRIEISTQSG
ASGWVKHASATLARHDASDSDAPRPAVEEAGAPTDELDPEQLYQRLRGAG
QQHGPAFRGIVGLAVTESGAARADVRLPSSARIGYRGFALHPVMMDIAVQ
TLGATRMALELAEQQDSGHTLVLPIRFAGIHVYGDIAEGVRAIGSLAATD
RPDRLVGRVTLVDPDGQPLLVIDEVEMAVLGSSASPTELTSRLFTLEWEP
KPLDQTAATPGAVLLIGDLGADDRLLPALQTSLTGSVAELDVVSPADAAK
LRAAITRTDARWQDIVVVCPPRAVDEALPQDAQLDLTQQRTLMIADVAQT
VTRMGARNSPRLWIVTRGAQQLSPADEVTLAQTQLRGIARVLTFEHPELK
TTLVDIEGDGEGSLTALTQELLAGADDDEISLRDGQRFVHRLVAAPTVGT
GDLELESRRTVVNLDAGGAVQLRTDQPGRLDSLTVHQVKRCRPQGDQVEV
RVAAAGLNFSDVLKAMGVYPGLDGAAPVIGGECVGYVTAIGDDVDSLEIG
QRVIAFGPGTFGSHLGTIADLVVPIPDTLPDNEAATFGIAYLTAWHSLCE
VGRLSPGERVLIHSATGGVGMAAVSIAKMIGARIYTTAGSDAKREMLSSL
GVDYVGDSRTVDFADEILELTDGYGVDIVLNSLAGEAIQRGVQILAPGGR
FIELGKKDVHANANLGLAALAKSASFSVVDLDLNLKLQPAKYRELLQEIL
EHVADGALEVLPVTEFGLRDAADGFRLMASGKHTGKIVISIPDGGTVEAI
ASPPPEPLVSPEGGYLIVGGMGGLGFVVARWLAEQGAGLIVLNGRSEPSD
DVRAAIADLSSGGTRIEVVTGDIAEPGTAERLVQTVQNSGFRLAGVLHSA

-continued
MVLDDEIVLNMSESAARRVFTPKVAGSWRLHEATADLDLDWWLTFSSVAS
LLGAPGQGSYAAANSFVDGLVAYRRSLGLPAVGINWGPWAEVGRAQFFAD
LGVSMITVEQGLAAMQLVLSADRARTGVFILDARQWFQSFPAAAGSSLFS
KLQESTTPERRAGGAIRAELDALEGAAAAERPARLAAAIAGEIRAVLRST
EPIDVDRPMESLGLDSLMALELRNRLEASLGTTLPAALVWAYPTITDLAG
ALCERLDEPAGARSGADTGAGAGMFRALFRQAVEDDRYGEFLDVLAEASA
FRPQFASPEACSERLDPVLLAGGPTDRAEGRAVLVGCTGTAANGGPHEFL
RLSTSFQEERDFLAVPLPGYGTGTGTALLPADLDTALDAQARAILRAA
GDAPVVLLGHSGGALLAHELAFRLERAHGAPPAGIVLVDPYPPGHQEPIE
VWSRQLGEGLFAGELEPMSDARLLAMGRYARFLAGPRPGRSSAPVLLVRA
SEPLGDWQEERGDWRAHWDLPHTVADVPGDHFTMMRDHAPAVAEAVLSWL
DAIEGIEGAG*

The amino acid sequence of "ppsC-pikTE" is as follows:

(SEQ ID NO: 6)
MTATPDRRAVITDALRKIDDLSARLEIAEKAGTEPIAVVGMGCRFPGGVD
NPEQFWDLLHEGRSGIVRVPSQRWDADALYTDDHTLAGTICNREGGFLST
WEPSEFDAEFFSIPPREAAAMDPQQRLFLEVAWEALENAGIPPQTIRGTQ
TGVFVGVTAYDYMLMMSGAVRAEELDAYLLTGNSANFAAGRTAYLLGARG
PAMVLDTACSSSLVAIHLACQSLRWRETDMALVGGTNLLLSPGTSIACSR
WGMLSPEGQCKTFDADADGYVRSEGAGVVVLKRLSDAQRDGNRILAVVRG
SAVNQDGASSGVTVPNGPAQQALLAQALDSAKLTPADIDYIEAHGTGTPL
GDPIELDSLSKVFADREGREPLVLGAVKTNLGHLEAAAGIAGFMKSVLAV
GHGRIPRNLNFRQLTPHASEGVSRLTIATEEMEWPATDQPRRAGVSSFGV
SGTNAHVVIEQAPDPAPVPRDAAPAVSTLVVSGKTAQRVAATAAALADWM
EGPGSEVPLSDVAHTLNHHRARQPKFATVAAVDREQAITGLRALAAGEPA
TGVVGCPEKPLGPGTVFVYSGRGSQWAGMGRQLLADEPAFAAAIAELEPV
FLAEAGFSLHDVIADGKELEGIEQIQLGLIGMQLALTALWRHYGVTPDLV
IGHSMGEVAATVVAGALTPAEGLRVTATRSRLMAPLSGQGTMAMLELDAT
ATEALIAGYPEVTLAIYASPRQTVIAGPPQMIDELIEQVRAQNRFAGRVN
IEVAPHNPAMDALQPLMRSELADLTPRPPSIPIISTTYEDLESRPAFDAE
HWATNMRNPVRFQQAITHAFNGADTAHHTFIEISAHPLLTHAISETLAAS
QDSAQGETDSGASYLSIGTLQRDAHDTLTFHTNFNATHTTRGPQTPHPAE
PHPVLPTTPWQHGQHWISSTTASRYATGSHPLLGIGVTDPTNGTRVWESQ
LGPDLLWLSDHVIDDLCVLPGSAYAEVALAAAMDTFKDAEGDQGSADPAG
PDGSVASNAHQPWVIRELSLHQLLHVTDGTKLVTTLTGDEHTCRIEISTQ
SGASGWVKHASATLARHDASDSDAPRPAVEEAGAPTDELDPEQLYQRLRG
AGQQHGPAFRGIVGLAVTESGAARADVRLPSSARIGYRGFALHPVMMDIA
VQTLGATRMALELAEQQDSGHTLVLPIRFAGIHVYGDIAEGVRAIGSLAA
TDRPDRLVGRVTLVDPDGQPLLVIDEVEMAVLGSSASPTELTSRLFTLEW
EPKPLDQTAATPGAVLLIGDLGADDRLLPALQTSLTGSVAELDVVSPADA

-continued

```
AKLRAAITRTDARWQDIVVVCPPRAVDEALPQDAQLDLTQQRTLMIADVA

QTVTRMGARNSPRLWIVTRGAQQLSPADEVTLAQTQLRGIARVLTFEHPE

LKTTLVDIEGDGEGSLTALTQELLAGADDDEISLRDGQRFVHRLVAAPTV

GTGDLELESRRTVVNLDAGGAVQLRTDQPGRLDSLTVHQVKRCRPQGDQV

EVRVAAAGLNFSDVLKAMGVYPGLDGAAPVIGGECVGYVTAIGDDVDSLE

IGQRVIAFGPGTFGSHLGTIADLVVPIPDTLPDNEAATFGIAYLTAWHSL

CEVGRLSPGERVLIHSATGGVGMAAVSIAKMIGARIYTTAGSDAKREMLS

SLGVDYVGDSRTVDFADEILELTDGYGVDIVLNSLAGEAIQRGVQILAPG

GRFIELGKKDVHANANLGLAALAKSASFSVVDLDLNLKLQPAKYRELLQE

ILEHVADGALEVLPVTEFGLRDAADGFRLMASGKHTGKIVISIPDGGTVE

AIASPPPEPLVSPEGGYLIVGGMGGLGFVVARWLAEQGAGLIVLNGRSEP

SDDVRAAIADLSSGGTRIEVVTGDIAEPGTAERLVQTVQNSGFRLAGVLH

SAMVLDDEIVLNMSESAARRVFTPKVAGSWRLHEATADLDLDWWLTFSSV

ASLLGAPGQGSYAAANSFVDGLVAYRRSLGLPAVGINWGPWAEVGRAQFF

ADLGVSMITVEQGLAAMQLVLSADRARTGVFILDARQWFQSFPAAAGSSL

FSKLQESTTPERRAGGAIRAELDALEGAAAAERPARLAAAIAGEIRAVLR

STEPIDVDRPMESLGLDSLMALELRNRLEASLGTTLPAALVWAYPTITDL

AGALCERLDEPAGARSGADTGAGAGMFRALFRQAVEDDRYGEFLDVLAEA

SAFRPQFASPEACSERLDPVLLAGGPTDRAEGRAVLVGCTGTAANGGPHE

FLRLSTSFQEERDFLAVPLPGYGTGTGTGTALLPADLDTALDAQARAILR

AAGDAPVVLLGHSGGALLAHELAFRLERAHGAPPAGIVLVDPYPPGHQEP

IEVWSRQLGEGLFAGELEPMSDARLLAMGRYARFLAGPRPGRSSAPVLLV

RASEPLGDWQEERGDWRAHWDLPHTVADVPGDHFTMMRDHAPAVAEAVLS

WLDAIEGIEGAG*
```

Approximately $10^2$-$10^3$ metric tons of alkyl lactones are produced annually worldwide, largely from petrochemical feedstocks using expensive chemical syntheses. This present invention has one or more advantages over this current methodology. First, a wide variety of alkyl lactones, containing functional groups with varying regio- and stereochemistry and chain lengths, can be produced from a single renewable feedstock. In the current method, this would require different petrochemical feedstocks for each target lactone. Next, this present invention does not require use of any rare or expensive metals. Current methodology employs the use of Hafnium and Ruthenium-based catalysts. In any industrial intramolecular cyclization reaction, losing starting materials to non-productive intermolecular polymerization is a concern. Enzymatic catalysis holds the potential to out-perform any currently used chemical method. Finally, a consolidated process directly from glucose to alkyl lactones via endogenously produced and cyclized hydroxy fatty acids would eliminate the need for multiple synthetic steps and purifications, reducing production costs.

Alkyl lactones of shorter chain lengths (C7-C12) are useful as renewable fuels. Lactones are more hydrophobic than fatty acids or hydroxy fatty acids, and can therefore potentially be used as fuels without further processing. Gamma-valerolactone (C5) has been reported as a "green solvent" that aids in the breakdown of cellulosic biomass into simple sugars. Longer chain alkyl lactones can potentially be used for this same application, perhaps with better efficacy. Alkyl lactones are used in a wide variety of fine fragrances and consumer goods (such as, detergents, cosmetics, and the like) by the flavor and fragrance industry, and are broadly referred to as "musk" fragrances.

In some embodiments, the genetically modified host cell is transformed with one or more nucleic acid constructs encoding one or more of the alkyl lactone forming enzymes. In some embodiments, the genetically modified host cell is of a species wherein the genome of the wild-type host cell encodes the alkyl lactone forming enzymes. In some embodiments, the genetically modified host cell is of a species wherein the genome of the wild-type host cell does not have any one, any two, or all of the alkyl lactone forming enzymes.

The genetically modified host cell can be any microbe capable of production of the alkyl lactone in accordance with the methods of the invention. In various embodiments, the microbes have characteristics that allow them to produce higher levels of product.

In some embodiments, the host cell is yeast. Yeast host cells suitable for practice of the methods of the invention include, but are not limited to, *Yarrowia, Candida, Bebaromyces, Saccharomyces, Schizosaccharomyces* and *Pichia*, including engineered strains provided by the invention. In one embodiment, *Saccharomyces cerevisae* is the host cell. In one embodiment, the yeast host cell is a species of *Candida*, including but not limited to *C. tropicalis, C. maltosa, C. apicola, C. paratropicalis, C. albicans, C. cloacae, C. guillermondii, C. intermedia, C. lipolytica, C. panapsilosis* and *C. zeylenoides*. In one embodiment, *Candida tropicalis* is the host cell. In some embodiments, the yeast host cell is a non-oleaginous yeast. In some embodiments, the non-oleaginous yeast is a *Saccharomyces* species. In some embodiments, the *Saccharomyces* species is *Saccharomyces cerevisiae*. In some embodiments, the yeast host cell is an oleaginous yeast. In some embodiments, the oleaginous yeast is a *Rhodosporidium* species. In some embodiments, the *Rhodosporidium* species is *Rhodosporidium toruloides*.

In some embodiments the host is bacteria. Bacterial host cells suitable for practice of the methods of the invention include, but are not limited to, *Escherichia, Corynebacterium, Pseudomonas, Streptomyces*, and *Bacillus*. In some embodiments, the *Escherichia* cell is an *E. coli, E. albertii, E. fergusonii, E. hermanii, E. marmotae*, or *E. vulneris*. In some embodiments, the *Corynebacterium* cell is *Corynebacterium glutamicum, Corynebacterium kroppenstedtii, Corynebacterium alimapuense, Corynebacterium amycolatum, Corynebacterium diphtheriae, Corynebacterium efficiens, Corynebacterium jeikeium, Corynebacterium macginleyi, Corynebacterium matruchotii, Corynebacterium minutissimum, Corynebacterium renale, Corynebacterium striatum, Corynebacterium ulcerans, Corynebacterium urealyticum*, or *Corynebacterium uropygiale*. In some embodiments, the *Pseudomonas* cell is a *P. putida, P. aeruginosa, P. chlororaphis, P. fluorescens, P. pertucinogena, P. stutzeri, P. syringae, P. cremoricolorata, P. entomophila, P. fulva, P. monteilii, P. mosselii, P. oryzihabitans, P. parafluva*, or *P. plecoglossicida*. In some embodiments, the *Streptomyces* cell is a *S. coelicolor, S. lividans, S. venezuelae, S. ambofaciens, S. avermitilis, S. albus*, or *S. scabies*. In some embodiments, the *Bacillus* cell is a *B. subtilis, B. megaterium, B. licheniformis, B. anthracis, B. amyloliquefaciens*, or *B. pumilus*.

One can modify the expression of a gene encoding any of the enzymes taught herein by a variety of methods in accordance with the methods of the invention. Those skilled in the art would recognize that increasing gene copy number, ribosome binding site strength, promoter strength, and various transcriptional regulators can be employed to alter an enzyme expression level. The present invention provides a method of producing an alkyl lactone in a genetically modified host cell that is modified by the increased expression of one or more genes taught herein.

In other embodiments, the host cells are modified, or not modified, to secrete the alkyl lactone into the growth medium. In other embodiments, the host cells are modified, or not modified, to accumulate alkyl lactone in the host cell. In these embodiments, the alkyl lactone is separated from the host cell by any suitable means, such as centrifugation or settling of the cell material, cell lysis, and subsequent purification of the alkyl lactone.

In some embodiments, the nucleic acid are recombinant DNA vectors.

It is to be understood that, while the invention has been described in conjunction with the preferred specific embodiments thereof, the foregoing description is intended to illustrate and not limit the scope of the invention. Other aspects, advantages, and modifications within the scope of the invention will be apparent to those skilled in the art to which the invention pertains.

All patents, patent applications, and publications mentioned herein are hereby incorporated by reference in their entireties.

The invention having been described, the following examples are offered to illustrate the subject invention by way of illustration, not by way of limitation.

The term "caprolactone derivative" includes all chemical species of the following structures:

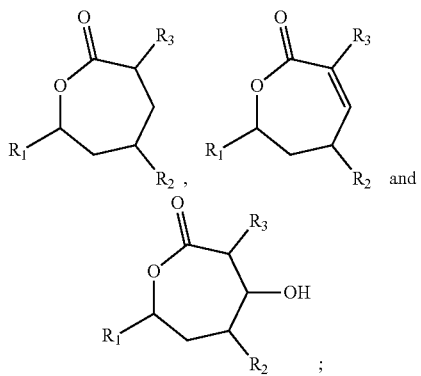

including, but not limited to, wherein R$_1$ is -methyl, -ethyl, -n-propyl, -isopropyl, -2-methylbutyryl or -sec-butyryl, -3-methylbutyryl or -isobutyryl, -n-butyl, or any straight or branched hydrocarbon chain comprising 4-10 carbons; R$_2$ is —H, —CH$_3$, or —CH$_2$CH$_3$; and, R$_3$ is —H, —CH$_3$, or —CH$_2$CH$_3$. In some embodiments, the "caprolactone derivative" is any one of the following

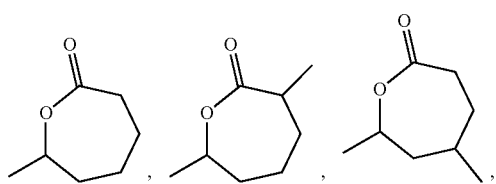

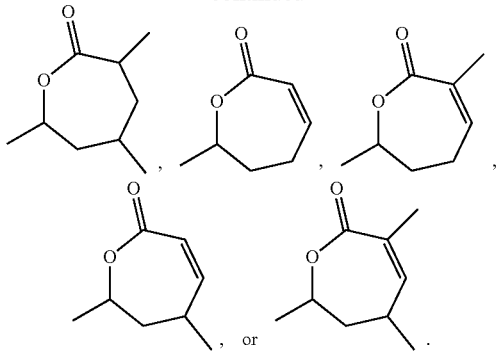

In some embodiments, the "caprolactone derivative" is useful as a composition, or part thereof, for 3D printing.

Example 1

Production of Pentadecanolide, a C15 Alkyl Lactone, from 15-Hydroxypentanoic Acid The proteins vhAAS and acpP-zeaTE were expressed in E. coli and purified using Ni-NTA affinity chromatography. To a solution of 100 µM 15-hydroxy pentadecanoic acid, we added adenosine triphosphate (1 mM), vhAAS enzyme (1 µM) and acpP-zeaTE enzyme (1 µM). The components were mixed and incubated at 30° C. for 16 hours. After incubation, the reaction mixture was extracted with an equal volume of ethyl acetate. The ethyl acetate solution was separated from the aqueous fraction and analyzed by GCMS analysis. We observed an increase in the concentration of pentadecanolide in the samples containing both vhAAS and acpP-zeaTE.

Figure 13:
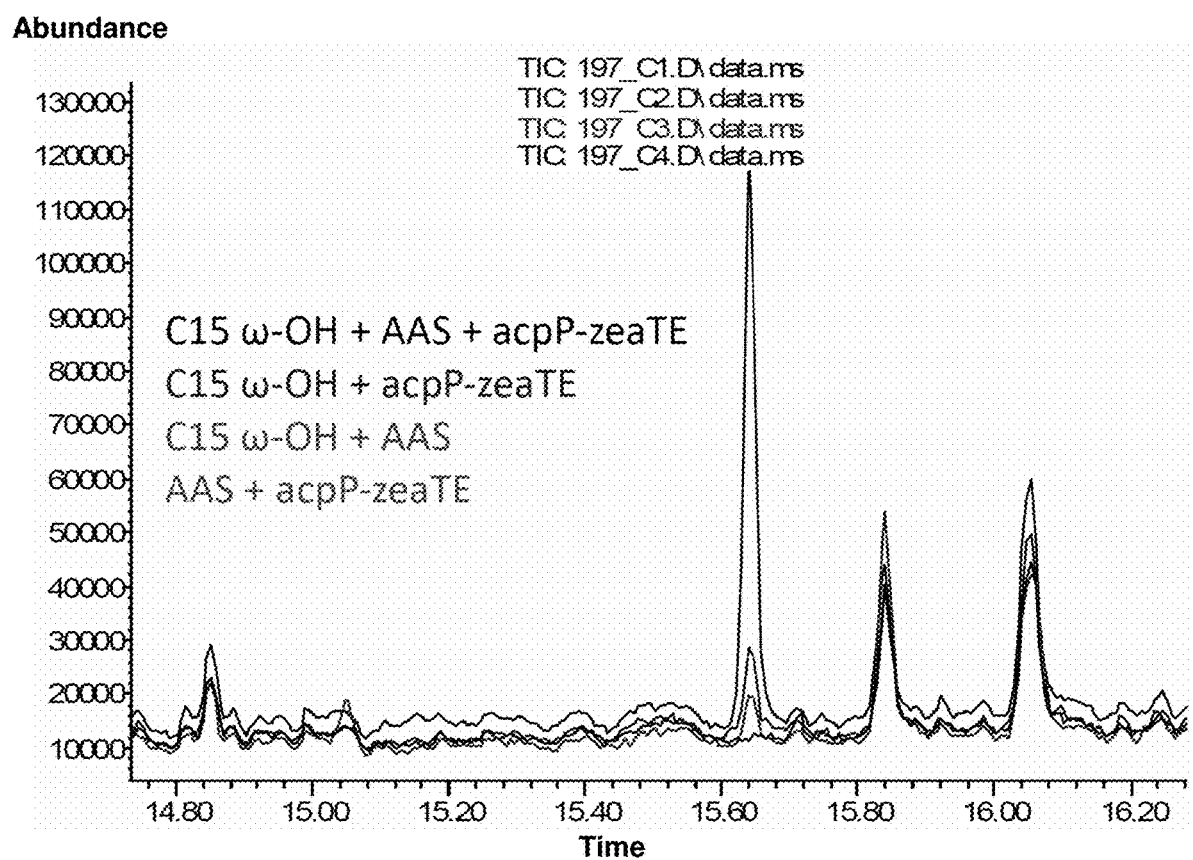
FIG. 13 shows the GCMS traces of in vitro reactions containing 15-hydroxydecanoic acid (C15 ω-OH), ATP, and combinations of enzymes in Example 1.
Figure 14:
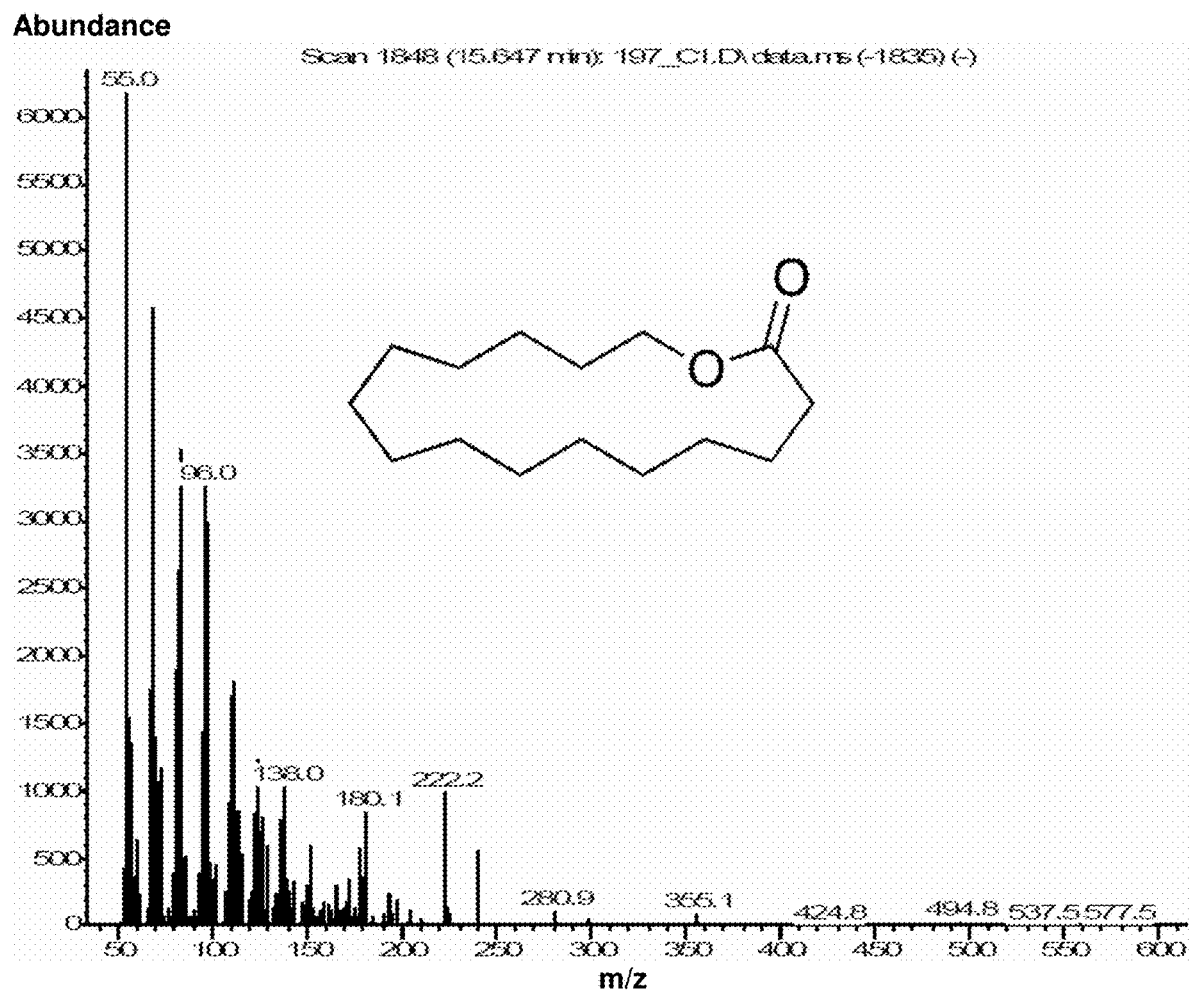
FIG. 14 shows the mass spectrum of the peak at 15.64 minutes confirming the identity of the product in Example 1.

FIG. 13 shows the GCMS traces of in vitro reactions containing 15-hydroxydecanoic acid (C15 ω-OH), ATP, and combinations of enzymes. FIG. 14 shows the mass spectrum of the peak at 15.64 minutes confirming the identity of the product.

Example 2

Production of Isobutyl Hexanoate and Pentyl Hexanoate

It is known that microbes can be engineered to produce various alkyl alcohols, including ethanol, n-propanol, isopropanol, n-butanol, isobutanol, 2-methylbutanol, n-pentanol, isopentanol, hexanol and octanol. If the non-natural fusion proteins claimed in this invention are expressed in combination with an AAS enzyme and any of these alcohol production pathways known to those skilled in the art, one can produce alkyl esters instead of alkyl lactones.

We dissolved 100 µM hexanoic acid 100 mM sodium phosphate. Adenosine triphosphate, isobutanol, vhAAS and acpP-zeaTE were added to the reaction and incubated at 30° C. for 16 hours. After incubation the reaction was extracted with an equal volume of ethyl acetate and the ethyl acetate layer was analyzed by GCMS. We observed a peak corresponding to isobutyl hexanoate in the presence of adenosine triphosphate, isobutanol, vhAAS and acpP-zeaTE.

We dissolved 100 µM hexanoic acid 100 mM sodium phosphate. Adenosine triphosphate, n-pentanol, vhAAS and acpP-zeaTE were added to the reaction and incubated at 30° C. for 16 hours. After incubation the reaction was extracted with an equal volume of ethyl acetate and the ethyl acetate layer was analyzed by GCMS. We observed a peak corresponding to pentyl hexanoate in the presence of adenosine triphosphate, isobutanol, vhAAS and acpP-zeaTE.

Figure 15:
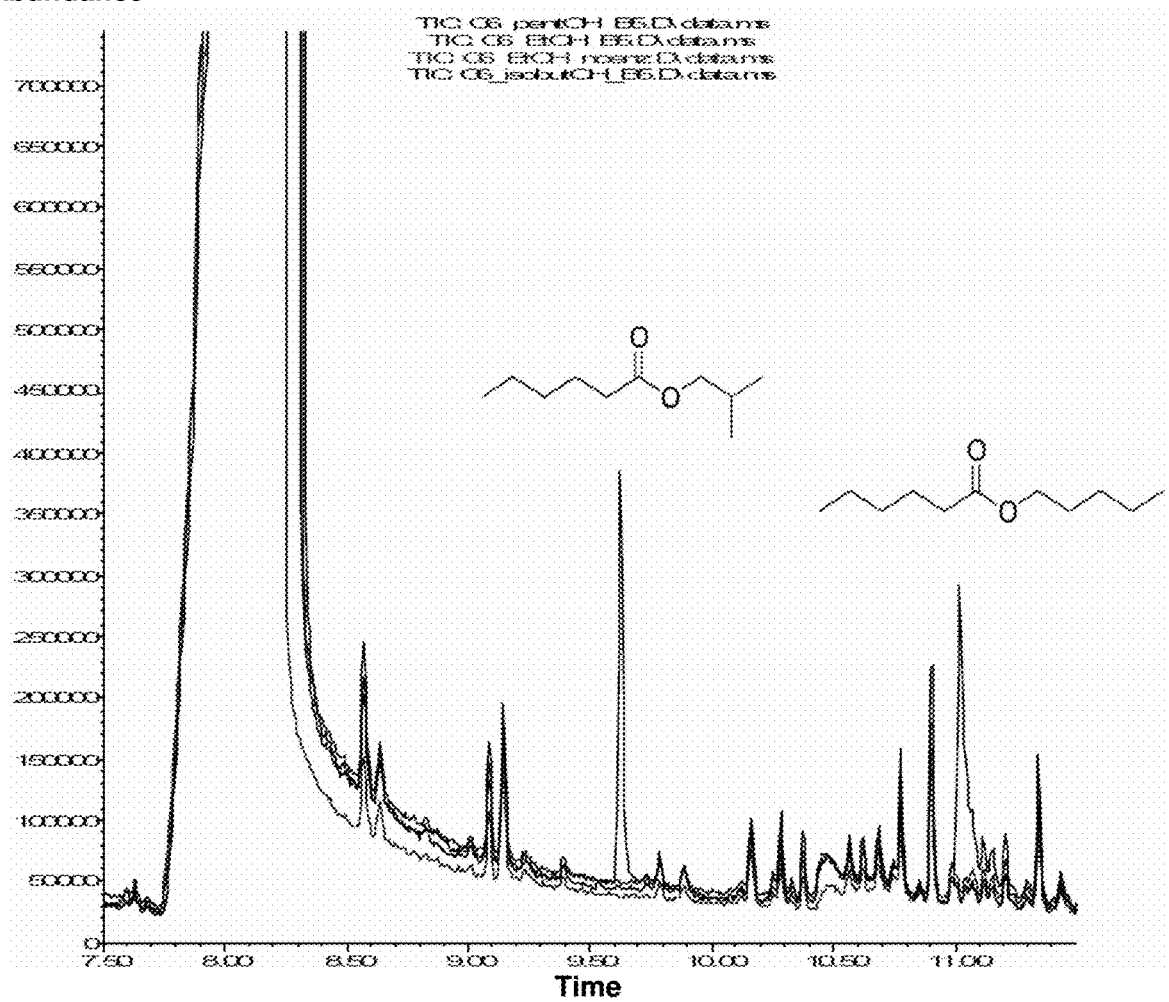
FIG. 15 shows GCMS chromatograms of alkyl esters produced by vhAAS and acpP-zeaTE in Example 2.

FIG. 15 shows GCMS chromatograms of alkyl esters produced by vhAAS and acpP-zeaTE.

Example 3

Production of 5-Hydroxydecanoic Acid and 5-Hydroxydodecanoic Acid

The non-natural fusion enzymes LipLM-ppsA, LipLM-ppsB, ppsBC-pikTE and ppsC-pikTE were expressed and purified from *Escherichia coli* using established molecular biology and biochemical methods.

a) 500 uM malonyl-coenzyme A and 1 mM nicotinamide adenine dinucleotide phosphate was dissolved in 100 mM sodium phosphate buffer pH 7.4. We added 100 µM octanoyl-coenzyme A, lipLM-ppsA and ppsBC-pikTE to this mixture and incubated at 30° C. for 16 hours. After incubation, an equal volume of methanol was added to the reaction mixture and the solution was analyzed by LCMS-TOF. The contents of this reaction were compared with an authentic standard of 5-hydroxydodecanoic acid and showed an identical mass and retention time.

b) 500 µM malonyl-coenzyme A and 1 mM nicotinamide adenine dinucleotide phosphate was dissolved in 100 mM sodium phosphate buffer pH 7.4. We added 100 µM octanoyl-coenzyme A, lipLM-ppsB and ppsC-pikTE to this mixture and incubated at 30° C. for 16 hours. After incubation, an equal volume of methanol was added to the reaction mixture and the solution was analyzed by LCMS-TOF. The contents of this reaction were compared with an authentic standard of 5-hydroxydodecanoic acid and showed an identical mass and retention time.

c) 500 uM malonyl-coenzyme A and 1 mM nicotinamide adenine dinucleotide phosphate was dissolved in 100 mM sodium phosphate buffer pH 7.4. We added 100 µM hexanoyl-coenzyme A, lipLM-ppsA and ppsBC-pikTE to this mixture and incubated at 30° C. for 16 hours. After incubation, an equal volume of methanol was added to the reaction mixture and the solution was analyzed by LCMS-TOF. The contents of this reaction were compared with an authentic standard of 5-hydroxydecanoic acid and showed an identical mass and retention time.

d) 500 µM malonyl-coenzyme A and 1 mM nicotinamide adenine dinucleotide phosphate was dissolved in 100 mM sodium phosphate buffer pH 7.4. We added 100 µM hexanoyl-coenzyme A, lipLM-ppsB and ppsC-pikTE to this mixture and incubated at 30° C. for 16 hours. After incubation, an equal volume of methanol was added to the reaction mixture and the solution was analyzed by LCMS-TOF. The contents of this reaction were compared with an authentic standard of 5-hydroxydecanoic acid and showed an identical mass and retention time.

LCMS chromatograms showed the production of hydrolyzed delta dodecalactone for a) and b), and hydrolyzed delta decalactone for c) and d).

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A genetically modified host cell comprising: a chimeric fusion comprising (a) (i) an acyl-acyl-carrier protein synthetase (AAS), fatty acyl-AMP ligase (FAAL), or fatty acyl-coenzyme A ligase (FACL) which converts a carboxyl of a hydroxy fatty acid into a thioester, and (ii) an esterase or thioesterase which converts the thioester into an alkyl lactone, or (b) (i) a FACL which converts the hydroxy fatty acid into a coenzyme A-bound thioester, and (ii) a mycobacteria PapA5 or wax ester synthase which converts the coenzyme A-bound thioester into an alkyl lactone; wherein the genetically modified host cell is a *Saccharomyces, Escherichia, Corynebacterium, Pseudomonas, Streptomyces*, and *Bacillus* cell.

2. The genetically modified host cell of claim 1, wherein the hydroxy fatty acid is a saturated hydroxy fatty acid or an unsaturated hydroxy fatty acid.

3. The genetically modified host cell of claim 2, wherein the saturated

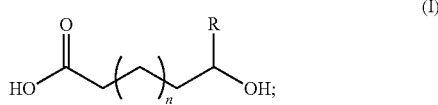

(I)

hydroxy fatty acid has the following chemical structure: wherein n is an integer from one to 20, and R is -H or an akyl chain having a chain length of C1 to C10.

4. The genetically modified host cell of claim 3, wherein n is an integer from one to 14.

5. The genetically modified host cell of claim 2, wherein the unsaturated

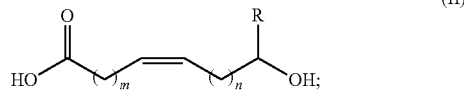

(II)

hydroxy fatty acid has the following chemical structure:
wherein m is an integer from one to 20, n is an integer from one to 20, and R is H or an akyl chain having a chain length of C1 to C10.

6. The genetically modified host cell of claim 5, wherein m is an integer from one to 14, n is an integer from zero to 13, and m+n=14.

7. The genetically modified host cell of claim 1, wherein the chimeric fusion comprises a cyclizing thioesterase (cycTE) enzyme.

8. The genetically modified host cell of claim 1, wherein the chimeric fusion comprises a mycobacteria PapA5, or a wax ester synthase enzyme.

9. The genetically modified host cell of claim 1, wherein host cell is a yeast or *Escherichia coli*.

10. The genetically modified host cell of claim 1, wherein host cell is capable of producing one or more alkyl lactone from glucose, acetate, propionate or glycerol, or a combination thereof.

11. The genetically modified host cell of claim 2, wherein the unsaturated hydroxy acid is polyunsaturated.

12. A genetically modified host cell comprising: a chimeric fusion comprising (i) an acyl-acyl-carrier protein synthetase (AAS), which converts a carboxyl of a hydroxy fatty acid into a thioester, and (ii) an esterase or thioesterase which converts the thioester into an alkyl lactone; wherein the genetically modified host cell is a yeast or cell, and the chimeric fusion comprises a *Vibrio harveyii* AAS depicted in SEQ ID NO:1 or a *Gibberella zeae* thioesterase depicted in SEQ ID NO:2.

13. The genetically modified host cell of claim 12, wherein the chimeric fusion comprises a *Gibberella zeae* thioesterase depicted in SEQ ID NO:2.

14. The genetically modified host cell of claim 12, wherein the chimeric fusion comprises a *Vibrio harveyii* AAS depicted in SEQ ID NO:1.

* * * * *